(12) United States Patent
Kubo

(10) Patent No.: US 10,944,947 B2
(45) Date of Patent: Mar. 9, 2021

(54) PROCESSOR DEVICE, METHOD OF OPERATING PROCESSOR DEVICE, ENDOSCOPE SYSTEM, IMAGE DISPLAY DEVICE, METHOD OF OPERATING IMAGE DISPLAY DEVICE, OPERATING PROGRAM FOR IMAGE DISPLAY DEVICE

(71) Applicant: FUJIFILM Corporation, Tokyo (JP)

(72) Inventor: Masahiro Kubo, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/714,296

(22) Filed: Dec. 13, 2019

(65) Prior Publication Data

US 2020/0120320 A1     Apr. 16, 2020

Related U.S. Application Data

(63) Continuation of application No. PCT/JP2018/021751, filed on Jun. 6, 2018.

(30) Foreign Application Priority Data

Jun. 14, 2017  (JP) .............................. JP2017-116548

(51) Int. Cl.
*H04N 9/64* (2006.01)
*H04N 9/04* (2006.01)
(Continued)

(52) U.S. Cl.
CPC ......... *H04N 9/643* (2013.01); *A61B 1/00045* (2013.01); *A61B 1/0653* (2013.01);
(Continued)

(58) Field of Classification Search
CPC ......... H04N 2005/2255; H04N 9/0455; H04N 5/2352; H04N 9/643; A61B 1/045;
(Continued)

(56) References Cited

U.S. PATENT DOCUMENTS

2008/0100702 A1    5/2008  Tannai
2010/0032546 A1    2/2010  Kawano et al.
(Continued)

FOREIGN PATENT DOCUMENTS

EP      2116176 A1    11/2009
JP   2008-113177 A     5/2008
(Continued)

OTHER PUBLICATIONS

The extended European search report issued by the European Patent Office dated May 27, 2020, which corresponds to European Patent Application No. 18816588.0-1122 and is related to U.S. Appl. No. 16/714,296.
(Continued)

*Primary Examiner* — Sherrie Hsia
(74) *Attorney, Agent, or Firm* — Studebaker & Brackett PC

(57) ABSTRACT

A processor device includes: an image acquisition unit that acquires a static image of an object to be observed; an embedding unit that embeds a correction profile, which is created by a creation unit according to tone change-related information about a change in the tone of the static image, in the static image; and an output unit that outputs the static image, in which the correction profile is embedded, to the outside. In an image display device, a static image in which a correction profile is embedded is received and correction is performed on the static image by using the correction profile. Then, the static image on which the subjected has been performed is displayed on a display.

17 Claims, 24 Drawing Sheets

(51) Int. Cl.
*H04N 5/235* (2006.01)
*A61B 1/00* (2006.01)
*A61B 1/06* (2006.01)
*H04N 5/225* (2006.01)

(52) U.S. Cl.
CPC ......... *H04N 5/2352* (2013.01); *H04N 9/0455* (2018.08); *H04N 2005/2255* (2013.01)

(58) Field of Classification Search
CPC ..... A61B 1/063; A61B 1/0653; A61B 1/0661; A61B 1/00045; A61B 1/06
USPC .......................... 348/65, 68–71, 74; 600/101
See application file for complete search history.

(56) References Cited

U.S. PATENT DOCUMENTS

| | | | |
|---|---|---|---|
| 2010/0073362 A1 | 3/2010 | Ikizyan | |
| 2011/0069164 A1* | 3/2011 | Ozawa | A61B 1/0638 348/68 |
| 2015/0087903 A1 | 3/2015 | Kuramoto | |
| 2015/0092090 A1 | 4/2015 | Miura | |
| 2017/0132811 A1 | 5/2017 | Yamaki | |

FOREIGN PATENT DOCUMENTS

| | | |
|---|---|---|
| JP | 2015-061569 A | 4/2015 |
| JP | 2015-066262 A | 4/2015 |
| JP | 2016-067708 A | 5/2016 |
| JP | 2016-174921 A | 10/2016 |
| WO | 2016/021285 A1 | 2/2016 |

OTHER PUBLICATIONS

International Search Report issued in PCT/JP2018/021751; dated Aug. 14, 2018.

International Preliminary Report on Patentability and Written Opinion issued in PCT/JP2018/021751; dated Dec. 17, 2019.

An Office Action; "Notice of Reasons for Refusal," mailed by the Japanese Patent Office dated Jan. 19, 2021, which corresponds to Japanese Patent Application No. 2019-525354 and is related to U.S. Appl. No. 16/714,296 with English language translation.

* cited by examiner

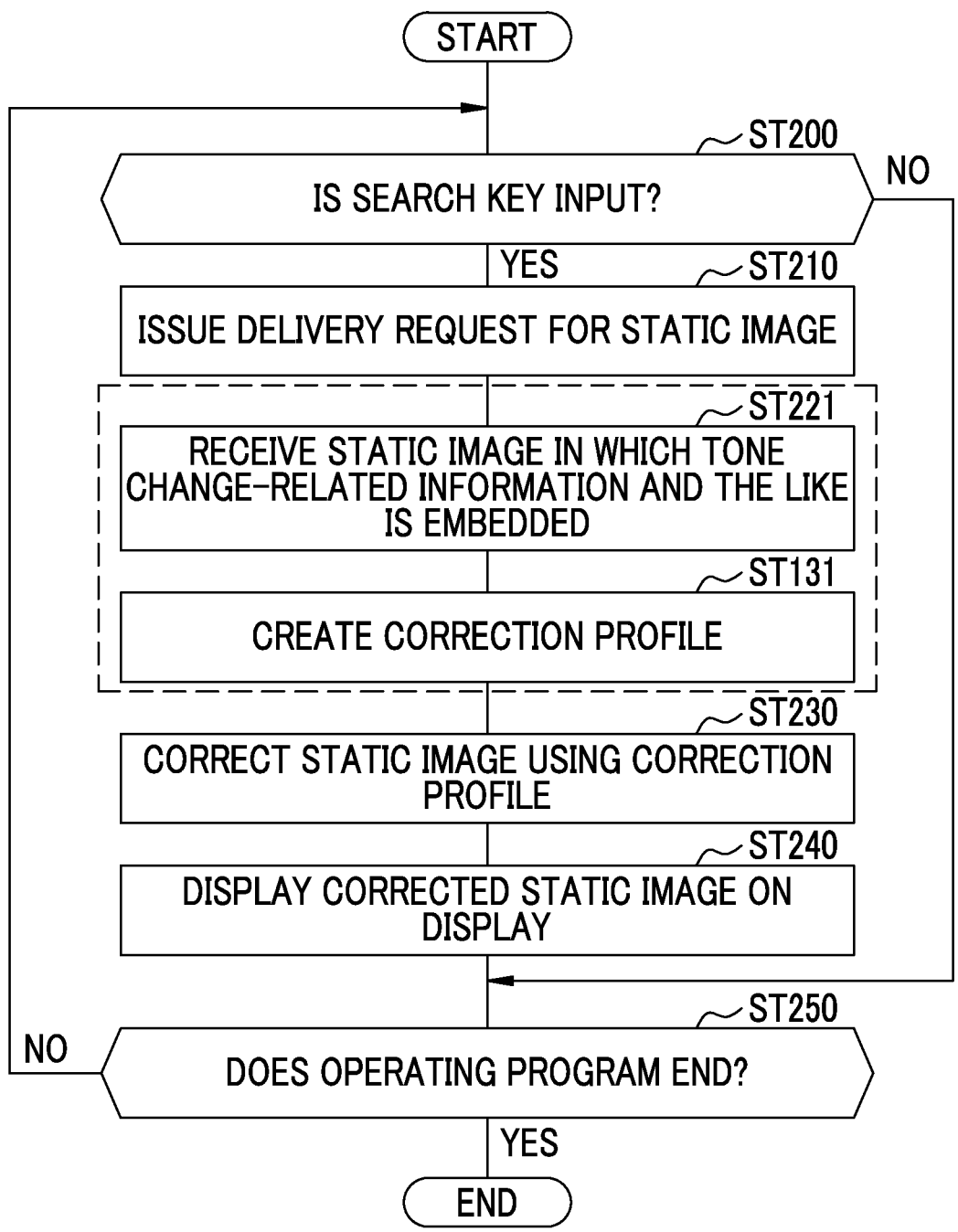

PROCESSOR DEVICE, METHOD OF OPERATING PROCESSOR DEVICE, ENDOSCOPE SYSTEM, IMAGE DISPLAY DEVICE, METHOD OF OPERATING IMAGE DISPLAY DEVICE, OPERATING PROGRAM FOR IMAGE DISPLAY DEVICE

CROSS-REFERENCE TO RELATED APPLICATIONS

This application is a Continuation of PCT International Application No. PCT/JP2018/021751 filed on 6 Jun. 2018, which claims priority under 35 U.S.C. § 119(a) to Japanese Patent Application No. 2017-116548 filed on 14 Jun. 2017. The above application is hereby expressly incorporated by reference, in its entirety, into the present application.

BACKGROUND OF THE INVENTION

1. Field of the Invention

The present invention relates to a processor device, a method of operating the processor device, an endoscope system, an image display device, a method of operating the image display device, and an operating program for the image display device.

2. Description of the Related Art

Endoscopy for observing an object to be observed, such as the surface of the stomach or the large intestine of an object to be examined (patient), with an endoscope is performed in a medical field. An endoscope includes an insertion part that is to be inserted into an object to be examined and an operation part that is provided on the proximal end side of the insertion part and is to be operated by an operator, such as an endoscopy technician. The distal end of the insertion part is provided with an image pickup element that picks up the image of an object to be observed. The operation part is provided with a release button that is used to record the image (static image) of an object to be observed.

The endoscope is connected to a light source device and a processor device, and the endoscope, the light source device, and the processor device form an endoscope system. A light source, which emits illumination light with which an object to be observed is to be illuminated, is built in the light source device. A semiconductor light source, for example, a light-emitting diode (hereinafter, abbreviated as an LED) is used as the light source. There is no semiconductor light source that has broad spectral characteristics covering the entire wavelength range of visible light, such as a xenon lamp or a metal halide lamp having been used as a light source in the related art. For this reason, a plurality of kinds of semiconductor light sources having different wavelength ranges, for example, three semiconductor light sources corresponding to a red, a green, and a blue are mounted on the light source device, which employs semiconductor light sources, to generate white light.

The image pickup element of the endoscope comprises color filters having a plurality of colors, for example, the respective colors of a red, a green, and a blue, and sequentially outputs image pickup signals, which correspond to the respective colors, to the processor device at a predetermined frame rate. The processor device performs various kinds of processing on the image pickup signals that correspond to the respective colors and are output from the image pickup element. Further, the image pickup signals subjected to the processing are sequentially output to a monitor as the video of the object to be observed. An operator observes the video on the monitor, and operates the release button as necessary to record the static image.

This kind of endoscope system has a problem that the tone of an image is changed in the related art. There are two causes of this problem. One of the two causes is a change in the wavelength of illumination light depending on the temperature of a semiconductor light source, such as an LED. In a case where the wavelength of illumination light is changed, the tone of the illumination light is also naturally changed and the tone of an image is eventually changed.

The other of the two causes is the individual difference of the light source of each light source device and the image pickup element of each endoscope. Specifically, the other of the two causes is a deviation in the spectral characteristics of illumination light and a deviation in the spectral characteristics of the color filters of the image pickup element. For example, the spectral characteristics of a color filter of an endoscope A are XA but the spectral characteristics of a color filter of an endoscope B are XB.

A case where the endoscope A is connected to a light source device of which the spectral characteristics of illumination light are Y and a case where the endoscope B is connected to a light source device of which the spectral characteristics of illumination light are Y are thought here. In the former case, an image has a tone corresponding to the spectral characteristics XA of the color filter of the endoscope A and the spectral characteristics Y of illumination light of the light source device. However, in the latter case, an image has a tone corresponding to the spectral characteristics XB of the color filter of the endoscope B and the spectral characteristics Y of illumination light of the light source device. That is, the tone of an image is changed between a case where the endoscope A is used and a case where the endoscope B is used.

JP2016-174921A is proposed for such a problem that the tone of an image is changed. In JP2016-174921A, a correction profile used to correct a change in the tone of an image is created according to the amount of drive (the amount of current) of a semiconductor light source, which is tone change-related information about a change in the wavelength of illumination light, and is applied to image pickup signals, which correspond to colors and are sequentially output from an image pickup element, in real time. Specifically, the correction profile includes matrix coefficients (described as first matrix coefficients in JP2016-174921A) to be multiplied by the image pickup signals corresponding to the respective colors.

Further, JP2016-174921A also discloses an aspect where a correction profile (described as second matrix coefficients in JP2016-174921A) corresponding to the spectral characteristics of illumination light and the spectral characteristics of color filters of an image pickup element is created and is applied to image pickup signals corresponding to the respective colors in real time.

SUMMARY OF THE INVENTION

Since a change in the wavelength of illumination light is not rapid, a change in the tone of an image, which is caused by a change in the wavelength of illumination light, is relatively gentle. For this reason, it is difficult for a change in the tone of an image to be recognized during endoscopy. Further, since an image cannot be compared with an image obtained from a combination of another endoscope having different spectral characteristics and the light source device during endoscopy, it is also difficult for a change in the tone of an image, which is caused by a deviation in the spectral characteristics of illumination light and a deviation in the spectral characteristics of the color filters of the image pickup element, to be recognized during endoscopy.

On the other hand, it is easy for a change in the tone of an image to be recognized in a case where a static image is observed using an image display device after endoscopy. That is, this case corresponds to a case where a static image obtained before a change in the wavelength of illumination light is compared with a static image obtained after a change in the wavelength of illumination light and a case where an image is compared with an image obtained from a combination of an endoscope having different spectral characteristics and the light source device. As described above, a change in the tone of an image does not become a problem much during endoscopy and becomes a problem in a case where a static image is observed after endoscopy.

However, in JP2016-174921A, a correction profile is created during endoscopy where a change in the tone of an image does not become a problem much and this correction profile is applied to the image pickup signals corresponding to the respective colors. Accordingly, resources are consumed in processing not having much necessity in JP2016-174921A.

An object of the invention is to provide a processor device that can allow a change in the tone of an image not to be noticeable with less wasteful processing, a method of operating the processor device, and an endoscope system.

Further, an object of the invention is to provide an image display device that can display an image where a change in tone is not noticeable, a method of operating the image display device, and an operating program for the image display device.

To achieve the object, a processor device of the invention is a processor device to which an endoscope irradiating an object to be observed with illumination light supplied from a light source is to be connected, and comprises a processor configured to function as an image acquisition unit, an embedding unit, and an output unit. The image acquisition unit acquires a static image of the object to be observed picked up according to an operator's instruction for operation. The embedding unit embeds tone change-related information about a change in a tone of the static image or a correction profile, which is created according to the tone change-related information and is used to correct a change in the tone, in the static image. The output unit outputs the static image, in which the tone change-related information or the correction profile is embedded, to the outside.

It is preferable that the tone change-related information is acquired only in a case where the instruction for operation is given. Further, it is preferable that the correction profile is created only in a case where the instruction for operation is given.

It is preferable that the tone change-related information is wavelength change-related information about a change in a wavelength of the illumination light depending on a temperature of the light source.

It is preferable that the tone change-related information is spectral characteristic information of the illumination light and spectral characteristic information of a color filter of an image pickup element picking up an image of the object to be observed.

It is preferable that the spectral characteristic information of the illumination light and the spectral characteristic information of the color filter are measured in advance and are stored in a memory.

It is preferable that the correction profile includes matrix coefficients to be multiplied by image pickup signals which correspond to a plurality of colors and are output from an image pickup element picking up an image of the object to be observed.

It is preferable that the correction profile is embedded in a standard color profile.

It is preferable that the light source is a light-emitting diode.

A method of operating a processor device of the invention is a method of operating a processor device to which an endoscope irradiating an object to be observed with illumination light supplied from a light source is to be connected, and comprises an image acquisition step, an embedding step, and an output step. The image acquisition step acquires a static image of the object to be observed picked up according to an operator's instruction for operation. The embedding step embeds tone change-related information about a change in a tone of the static image or a correction profile, which is created according to the tone change-related information and is used to correct a change in the tone, in the static image. The output step outputs the static image, in which the tone change-related information or the correction profile is embedded, to the outside.

An endoscope system of the invention comprises an endoscope that irradiates an object to be observed with illumination light supplied from a light source, a light source device in which the light source is built, and a processor device to which the endoscope and the light source device are to be connected. The processor device includes a processor configured to function as an image acquisition unit, an embedding unit, and an output unit. The image acquisition unit acquires a static image of the object to be observed picked up according to an operator's instruction for operation. The embedding unit embeds tone change-related information about a change in a tone of the static image or a correction profile, which is created according to the tone change-related information and is used to correct a change in the tone, in the static image. The output unit outputs the static image, in which the tone change-related information or the correction profile is embedded, to the outside.

An image display device of the invention comprises a processor configured to function as a receiving unit, a creation unit, a correction unit, and a display control unit. The receiving unit receives a static image in which tone change-related information about a change in a tone of the static image or a correction profile created according to the tone change-related information and used to correct a change in the tone is embedded. The creation unit creates the correction profile from the tone change-related information in a case where the static image received by the receiving unit is the static image in which the tone change-related information is embedded. The correction unit performs the correction the static image by using the correction profile. The display control unit controls display of the static image, on which the correction has been, on a display unit.

A method of operating an image display device of the invention comprises a receiving step, a creation step, a correction step, and a display control step. A static image in which tone change-related information about a change in a tone of the static image or a correction profile created according to the tone change-related information and used to correct a change in the tone is embedded is received in the receiving step. In the creation step, the correction profile is created from the tone change-related information in a case where the static image received in the receiving step is the static image in which the tone change-related information is embedded. In the correction step, the correction is performed on the static image by using the correction profile. Display of the static image, on which the correction has been performed, on a display unit is controlled in the display control step.

An operating program for an image display device of the invention causes a computer to perform a reception function, a creation function, a correction function, and a display control function. The reception function receives a static image in which tone change-related information about a change in a tone of the static image or a correction profile created according to the tone change-related information and used to correct a change in the tone is embedded. The creation function creates the correction profile from the tone change-related information in a case where the static image received by the reception function is the static image in which the tone change-related information is embedded. The correction function performs the correction on the static image by using the correction profile. The display control function controls display of the static image, on which the correction has been performed, on a display unit.

According to the invention, tone change-related information about a change in a tone of a static image or a correction profile, which is created according to the tone change-related information and is used to correct a change in the tone, is embedded in the static image and the static image is output to the outside. Accordingly, it is possible to provide a processor device that can allow a change in the tone of an image not to be noticeable with less wasteful processing, a method of operating the processor device, and an endoscope system.

Further, according to the invention, a static image, in which tone change-related information about a change in a tone of a static image or a correction profile created according to the tone change-related information and used to correct a change in the tone is embedded, is received; correction is performed on the static image by using the correction profile; and the static image on which the correction has been performed is displayed on a display unit. Accordingly, it is possible to provide an image display device that can display an image where a change in tone is not noticeable, a method of operating the image display device, and an operating program for the image display device.

BRIEF DESCRIPTION OF THE DRAWINGS

FIG. 27 is a flowchart showing the procedure of processing of the image display device of the third embodiment.

DESCRIPTION OF THE PREFERRED EMBODIMENTS

First Embodiment

Figure 1:
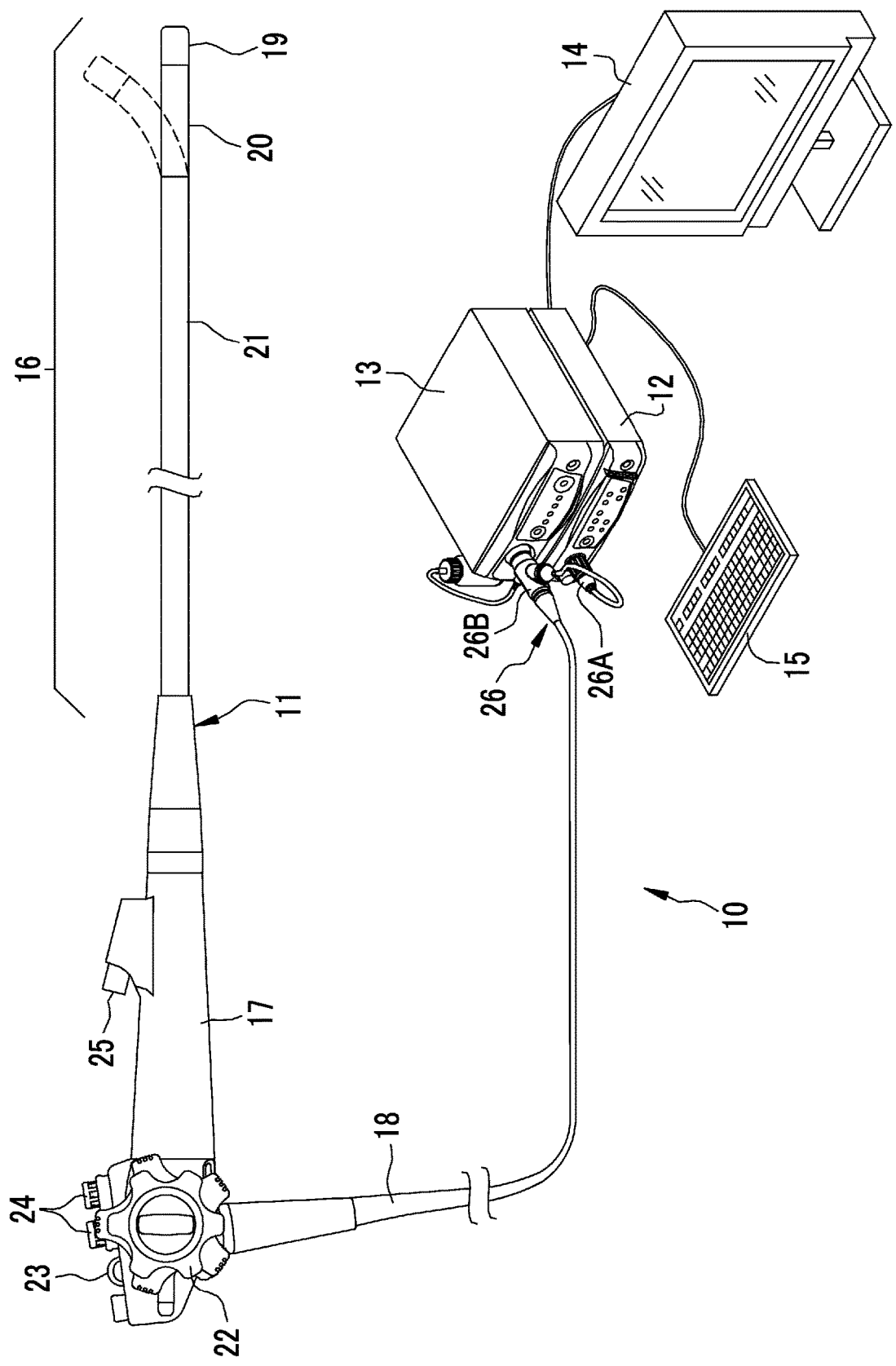
FIG. 1 is a diagram showing the appearance of an endoscope system.

In FIG. 1, an endoscope system 10 comprises an endoscope 11, a processor device 12, and a light source device 13. The endoscope 11 picks up the image of an object to be observed, which is present in an object to be examined, and outputs image pickup signals to the processor device 12. The processor device 12 generates the image of the object to be observed on the basis of the image pickup signals output from the endoscope 11, and outputs the generated image to the monitor 14. The light source device 13 supplies illumination light, with which the object to be observed is to be illuminated, to the endoscope 11.

An input unit 15, such as a keyboard and a mouse, is connected to the processor device 12 in addition to the monitor 14. The input unit 15 is operated by an operator in a case where information about the object to be examined is to be input, and the like.

The endoscope 11 comprises an insertion part 16 that is to be inserted into an object to be examined, an operation part 17 that is provided on the proximal end side of the insertion part 16 and is to be operated by an operator, and a universal cord 18 that extends from the lower end of the operation part 17.

The insertion part 16 includes a distal end part 19, a bendable part 20, and a flexible tube part 21; and the distal end part 19, the bendable part 20, and the flexible tube part 21 are connected in this order from the distal end side. The bendable part 20 is formed of a plurality of connected bendable pieces, and is bendable in a vertical direction and a lateral direction. The upward bending of the bendable part is shown in FIG. 1 by a broken line. The flexible tube part 21 has flexibility that allows the flexible tube part 21 to be inserted into a convoluted tubular organ, such as the esophagus or the intestine.

A communication cable that transmits reference clock signals used to drive an image pickup element 46 (see FIG. 4) and image pickup signals output from the image pickup element 46, a light guide 45 (see FIG. 4) that guides illumination light supplied from the light source device 13 to illumination windows 31 (see FIG. 2), and the like are inserted into the insertion part 16.

The operation part 17 is provided with an angle knob 22, a release button 23, an air/water supply button 24, a forceps port 25, and the like. The angle knob 22 is rotationally operated in a case where an operator is to bend the bendable part 20 in the vertical direction or the lateral direction to make the distal end part 19 face in a desired direction. The release button 23 is operated to be pressed in a case where the image (static image) of the object to be observed is to be recorded. The air/water supply button 24 is operated in a case where air and water are supplied from an air/water supply nozzle 32 (see FIG. 2). Various treatment tools, such as an electric scalpel, are inserted into the forceps port 25. The operation part 17 is provided with a mode changeover switch that is operated in a case where two observation modes of a normal observation mode and a special observation mode to be described later are to be switched, a zoom operation button that is used to move a zoom lens of an objective optical system 50 (see FIG. 4) along an optical axis to perform optical zoom, and the like, in addition to these.

The communication cable and the light guide 45, which extend from the insertion part 16, are inserted into the universal cord 18. A connector 26 is provided at one end of the universal cord 18 that faces the processor device 12 and the light source device 13 provided on the side opposite to the operation part 17. The connector 26 is a composite connector that includes a connector 26A for communication and a connector 26B for a light source. The connector 26A for communication is attachably and detachably connected to the processor device 12, and the connector 26B for a light source is attachably and detachably connected to the light source device 13.

Figure 2:
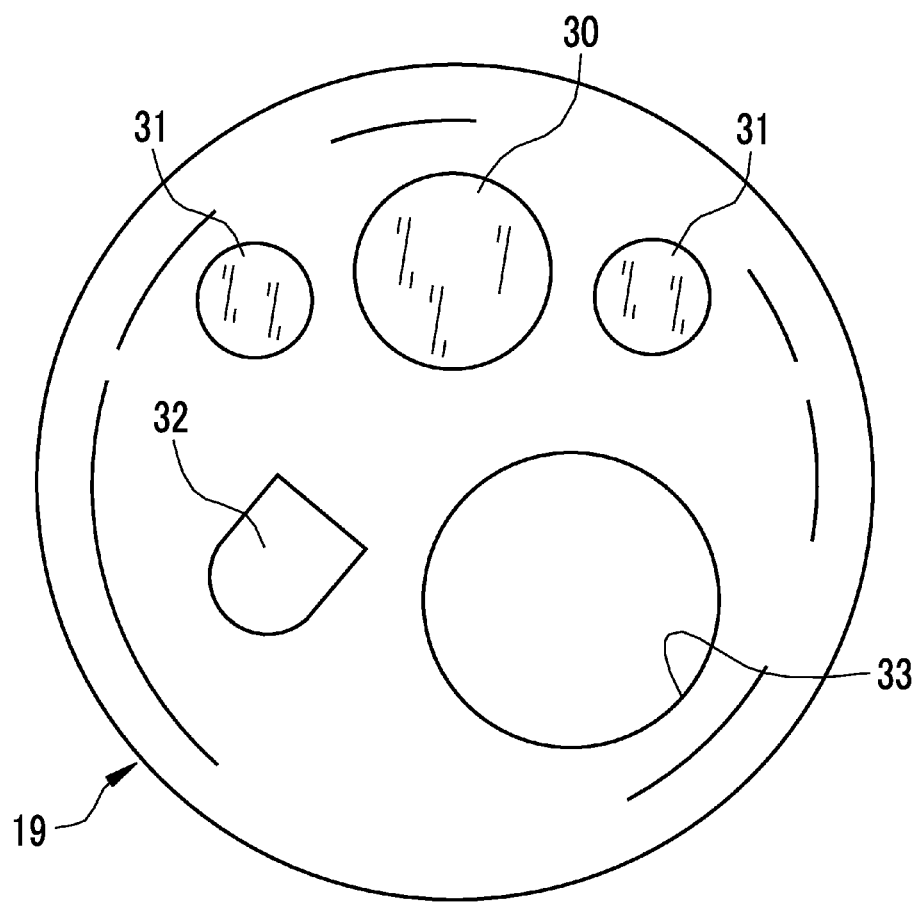
FIG. 2 is a front view of a distal end part of an endoscope.

In FIG. 2, the distal end face of the distal end part 19, which faces the object to be observed, is provided with an observation window 30 that is positioned in the middle on the upper side, a pair of illumination windows 31 that is provided at positions on both sides of the observation window 30, an air/water supply nozzle 32 of which the opening faces the observation window 30, and a forceps outlet 33. The object to be observed is irradiated with illumination light, which is supplied from the light source device 13, through the illumination windows 31. The image of the object to be observed, which is irradiated with the illumination light, is taken from the observation window 30. Air and water are ejected to the observation window 30 from the opening of the air/water supply nozzle 32, so that the observation window 30 is cleaned. The distal ends of various treatment tools inserted into the forceps port 25 protrude from the forceps outlet 33.

Figure 3:
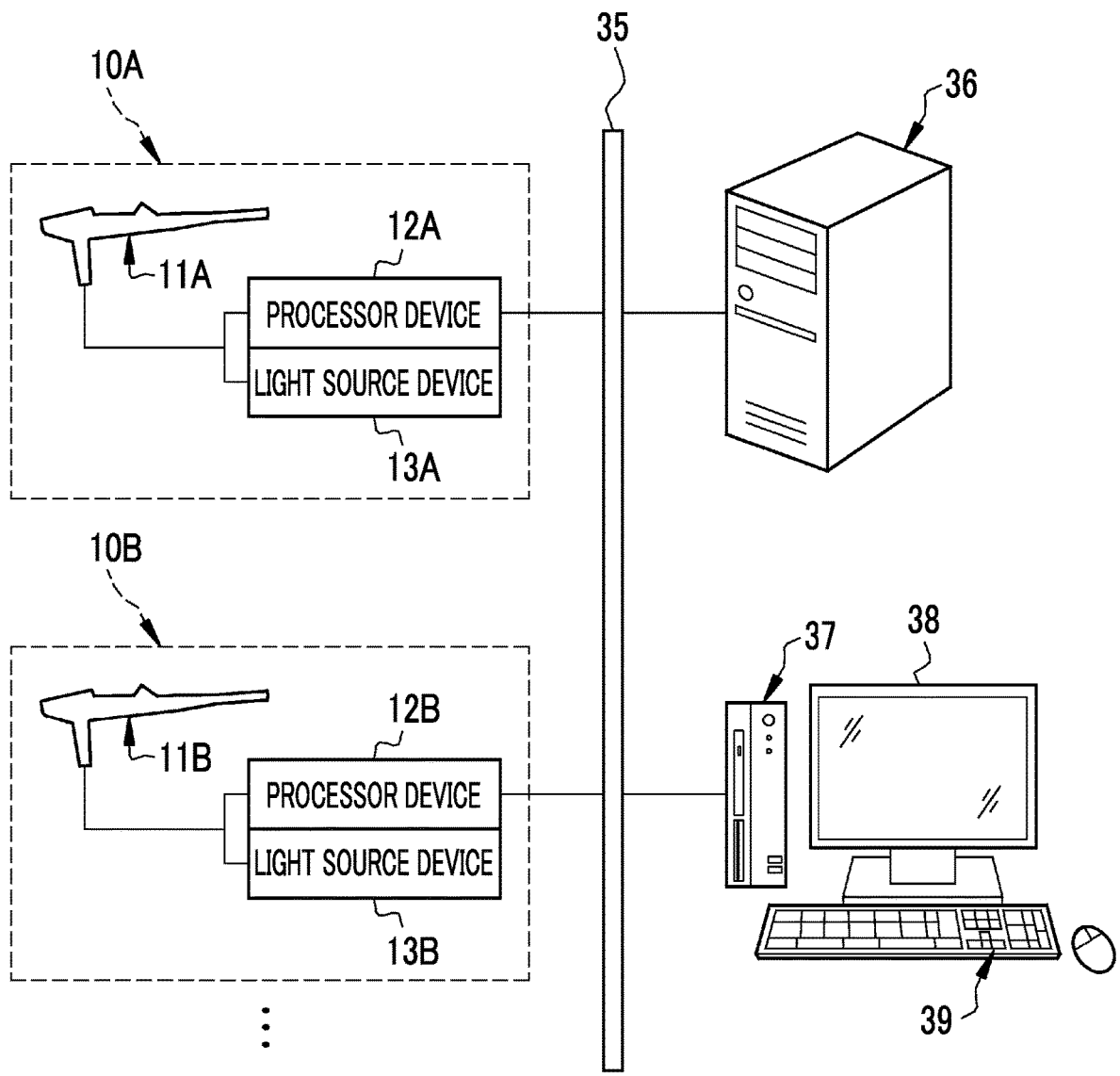
FIG. 3 is a diagram showing endoscope systems, an image storage server, and an image display device.

In FIG. 3, a plurality of endoscope systems 10, such as endoscope systems 10A, 10B, . . . , are installed in a medical facility. For example, each of the endoscope systems 10A, 10B, . . . is provided in each of a plurality of endoscopy rooms of a medical facility. The respective processor devices 12A, 12B, . . . and the respective light source devices 13A, 13B, . . . of the respective endoscope systems 10A, 10B, . . . are shared by the endoscopes 11A, 11B, . . . of the respective endoscope systems 10A, 10B, . . . . That is, the endoscope 11A of the endoscope system 10A may be used while being connected to the processor device 12B and the light source device 13B of the endoscope system 10B.

The respective processor devices 12A, 12B, . . . are connected to a network 35, such as a local area network (LAN), built in the medical facility. An image storage server 36 and an image display device 37 are connected to the network 35.

The respective processor devices 12A, 12B, . . . transmit the static images of objects to be observed to the image storage server 36 through the network 35. The image storage server 36 is a server computer, and stores the static images transmitted from the respective processor devices 12A, 12B, . . . . The image storage server 36 searches for a desired static image according to a delivery request for a static image transmitted from the image display device 37, and delivers the searched static image to the image display device 37 through the network 35.

The image display device 37 is a desktop personal computer, and is operated by a medical doctor of a diagnosis and treatment department having given an order for endoscopy. The image display device 37 includes a display 38 and an input unit 39, such as a keyboard and a mouse. The display 38 corresponds to a display unit, and displays the static image delivered from the image storage server 36. The input unit 39 is operated in a case where the delivery of a static image is to be requested.

Although only one image storage server 36 and only one image display device 37 are shown in FIG. 3, a plurality of image storage servers and a plurality of image display devices may be installed as with the endoscope systems 10A, 10B, . . . . As long as the respective endoscope systems and the respective processor devices do not need to be particularly distinguished from each other, alphabets, such as A and B, used to distinguish the respective endoscope systems and the respective processor devices will be omitted below.

Figure 4:
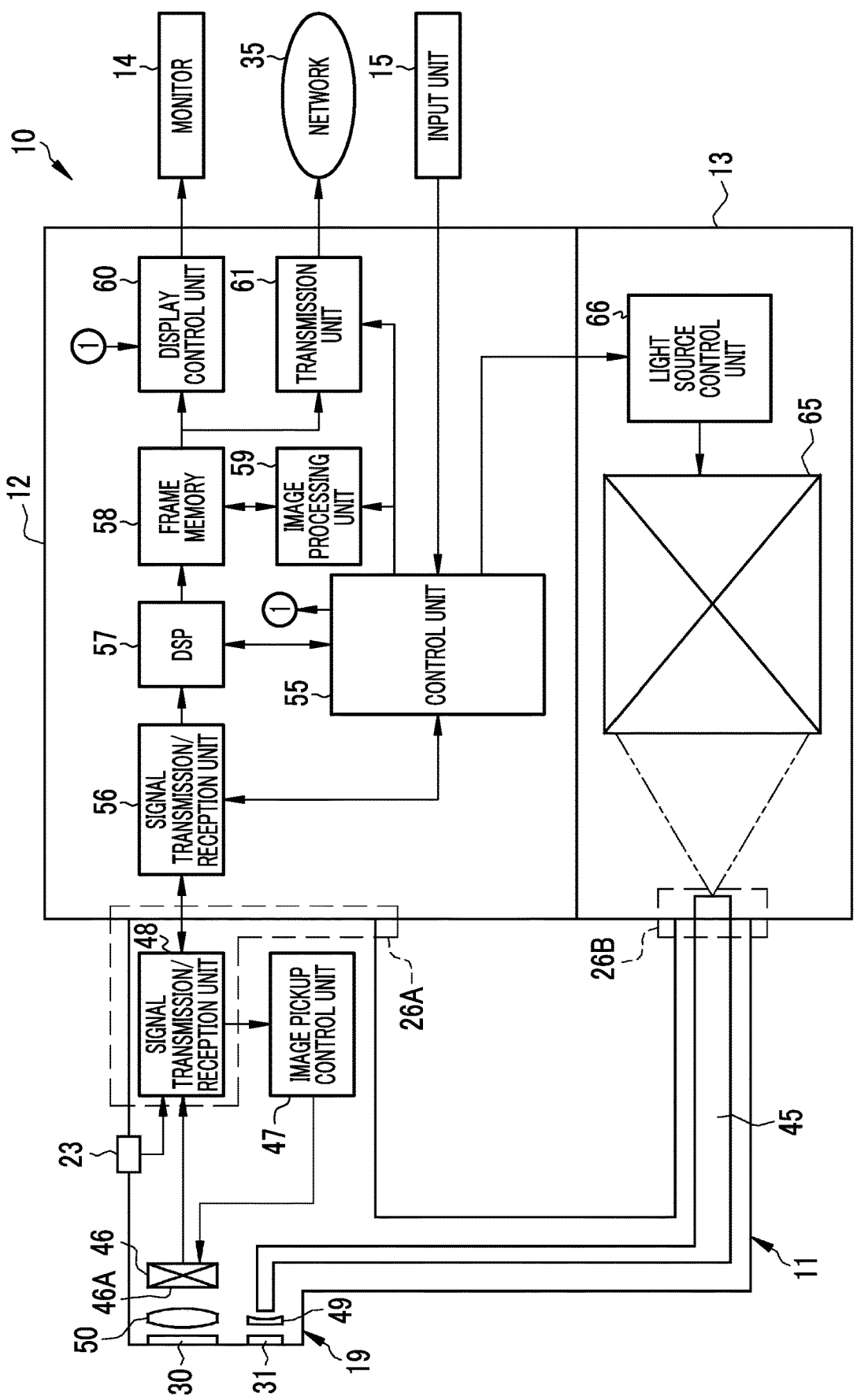
FIG. 4 is a block diagram of the endoscope system.

In FIG. 4, the endoscope 11 comprises a light guide 45, an image pickup element 46, an image pickup control unit 47, and a signal transmission/reception unit 48. The light guide 45 is formed of a bundle of a plurality of optical fibers, and guides illumination light, which is supplied from the light source device 13, to the illumination windows 31. In a case where the connector 26B for a light source is connected to the light source device 13, an incident end of the light guide 45 disposed in the connector 26B for a light source faces a light source unit 65 of the light source device 13. On the other end, an emission end of the light guide 45 positioned at the distal end part 19 branches into two emission ends on the near side of the illumination windows 31 so that illumination light is guided to the pair of illumination windows 31.

Irradiation lenses 49 are disposed at the back of the illumination windows 31. The emission ends of the light guide 45 are disposed at positions that face the irradiation lenses 49. Illumination light supplied from the light source device 13 is guided to the irradiation lenses 49 by the light guide 45, and the object to be observed is irradiated with the illumination light from the illumination windows 31. The irradiation lens 49 is formed of a concave lens, and increases the divergence angle of light to be emitted from the light guide 45. Accordingly, the wide range of the object to be observed can be irradiated with illumination light.

The objective optical system 50 and the image pickup element 46 are disposed at the back of the observation window 30. The image of the object to be observed is incident on the objective optical system 50 through the observation window 30, and is formed on an image pickup surface 46A of the image pickup element 46 by the objective optical system 50.

The image pickup element 46 is, for example, a charge coupled device (CCD) type image pickup element. A plurality of photoelectric conversion elements, such as photo-diodes, which form pixels, are arrayed on the image pickup surface 46A of the image pickup element 46 in the form of a matrix. The photoelectric conversion element of each pixel photoelectrically converts received light, and stores a signal charge corresponding to the amount of received light thereof. The signal charge is converted into a voltage signal by an amplifier, and is read out. The voltage signal is subjected to noise removal, analog/digital conversion, and the like, and is input to the signal transmission/reception unit 48 as a digital image pickup signal.

The image pickup control unit 47 controls the drive of the image pickup element 46. Specifically, the image pickup control unit 47 inputs driving signals to the image pickup element 46 in synchronization with reference clock signals that are input from a control unit 55 of the processor device 12 through the signal transmission/reception unit 48. The image pickup element 46 sequentially outputs image pickup signals at a predetermined frame rate, for example, 60 frames/sec on the basis of the driving signals input from the image pickup control unit 47.

The signal transmission/reception unit 48 is provided in the connector 26A for communication. The signal transmission/reception unit 48 transmits and receives various signals to and from the processor device 12 by an optical transmission system that uses, for example, infrared light. The various signals also include a recording instruction signal for a static image generated by the operation of the release button 23, an operation signal (mode switching signal) of the mode changeover switch, an operation signal (zoom operation signal) of the zoom operation button, or the like in addition to the reference clock signals and the image pickup signals having been described above. The connector 26A for communication is provided with, for example, a power receiving unit, which receives power to be transmitted from the processor device 12 by a wireless power transmission system using magnetic-field resonance, in addition to the signal transmission/reception unit 48.

The processor device 12 comprises a control unit 55, a signal transmission/reception unit 56, a digital signal processor (DSP) 57, a frame memory 58, an image processing unit 59, a display control unit 60, and a transmission unit 61. The control unit 55 includes a central processing unit (CPU), a read only memory (ROM) that stores a control program and setting data required for control, a random access memory (RAM) that loads a program and functions as a working memory, and the like; and controls the respective parts of the processor device 12 in a case where the CPU executes the control program.

The signal transmission/reception unit 56 is the same as the signal transmission/reception unit 48 of the endoscope 11, and transmits and receives various signals to and from the endoscope 11 by an optical transmission system. The signal transmission/reception unit 56 transmits the reference clock signals, which are input from the control unit 55, to the signal transmission/reception unit 48. Further, the signal transmission/reception unit 56 receives the image pickup signals, which are output from the image pickup element 46, and the recording instruction signal, which is generated from the release button 23, from the signal transmission/reception unit 48; and outputs the image pickup signals to the DSP 57 and outputs the recording instruction signal to the control unit 55. The signal transmission/reception unit 56 also outputs the mode switching signal, the zoom operation signal, and the like to the control unit 55.

The DSP 57 performs well-known processing, such as pixel interpolation, gradation conversion, gamma correction, and white balance correction, on the image pickup signals. The DSP 57 outputs the image pickup signals, which have been subjected to the processing, to the frame memory 58.

Further, the DSP 57 calculates exposure values on the basis of the image pickup signals. Then, the DSP 57 outputs the calculated exposure values to the control unit 55. The control unit 55 transmits exposure control signals, which correspond to the exposure values, to a light source control unit 66 of the light source device 13. The DSP 57 performs the calculation and output of the exposure values at a predetermined sampling cycle that is equal to or longer than a frame rate.

The frame memory 58 stores image pickup signals that are output from the DSP 57 and image pickup signals that have been subjected to various kinds of image processing performed by the image processing unit 59. The display control unit 60 reads out the image pickup signals, which have been subjected to the image processing, from the frame memory 58; converts the image pickup signals into video signals, such as composite signals or component signals; and outputs the video signals to the monitor 14 as the image of the object to be observed.

The image processing unit 59 performs various kinds of image processing, such as color emphasis processing and structure emphasis processing, on the image pickup signals, which are subjected to processing by the DSP 57 and are output to the frame memory 58, and generates the image of the object to be observed. The image processing unit 59 generates an image whenever the image pickup signals stored in the frame memory 58 are updated. The images, which are generated by the image processing unit 59, are sequentially output to the monitor 14 through the display control unit 60 as a video.

The transmission unit 61 transmits the static image of the object to be observed to the outside through the network 35. In a case where a recording instruction signal is input to the control unit 55 from the signal transmission/reception unit 56, the control unit 55 temporarily stops the rewriting of the image pickup signals in the frame memory 58 that is performed by the DSP 57. The transmission unit 61 reads out the image pickup signals (having been subjected to image processing), of which the rewriting is temporarily stopped, from the frame memory 58, and transmits the image pickup signals to the image storage server 36 through the network 35 as the static image of the object to be observed. Time in which the rewriting of the image pickup signals is temporarily stopped is, for example, 1 to 3 seconds.

The light source device 13 comprises a light source unit 65 and a light source control unit 66. The light source unit 65 will be described in detail later with reference to FIG. 5, but includes four different kinds of LEDs 70, 71, 72, and 73 corresponding to a light source. The light source control unit 66 receives the exposure control signals transmitted from the control unit 55. Specifically, the exposure control signals are the amounts IR, IG, IB, and IV of driving current (see FIG. 16) of the respective LEDs 70 to 73. The amounts IR to IV of current are values that allow the amounts of light of the respective LEDs 70 to 73 to have predetermined intensities and ratios suitable for the observation of the object to be observed.

The light source control unit 66 continuously gives the amounts IR to IV of current, which are represented by the received exposure control signals, to the respective LEDs 70 to 73 to turn on the respective LEDs 70 to 73. The amounts IR to IV of current may be given in the form of a pulse without being continuously given to perform pulse amplitude modulation (PAM) control for changing the amplitude of a pulse or pulse width modulation (PWM) control for changing the duty ratio of a pulse.

Figure 5:
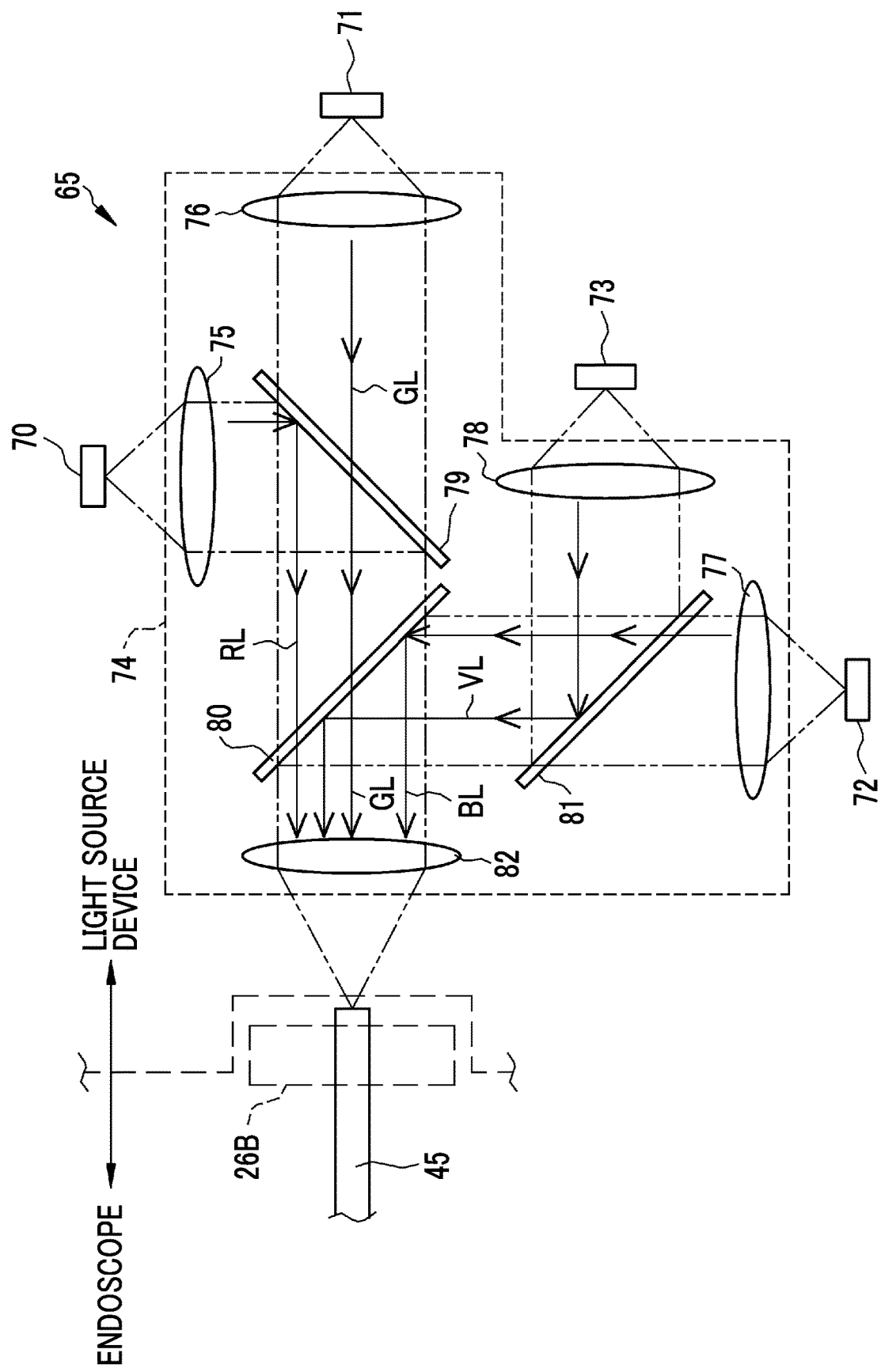
FIG. 5 is a diagram showing a light source unit.

In FIG. 5, the light source unit 65 includes the respective color LEDs 70 to 73 having a red, a green, a blue, and a violet and a light source optical system 74. The red LED 70 emits light in a red wavelength range (red light RL, see FIG. 6), the green LED 71 emits light in a green wavelength range (green light GL, see FIG. 7), the blue LED 72 emits light in a blue wavelength range (blue light BL, see FIG. 8), and the violet LED 73 emits light in a violet wavelength range (violet light VL, see FIG. 9).

The respective LEDs 70 to 73 is an LED in which a P-type semiconductor and an N-type semiconductor are joined to each other as well known. Further, in a case where a voltage is applied, electrons and holes are recombined with each other beyond a bandgap near a PN junction and current flows. Energy corresponding to a bandgap is emitted as light at the time of the recombination. The amounts of light to be emitted from the respective LEDs 70 to 73 are increased or decreased according to the increase or decrease of power to be supplied (here, the amounts IR to IV of current).

Further, the wavelength of light to be emitted from each of the LEDs 70 to 73 is changed according to a temperature change. For example, the peak wavelength of light to be emitted is shifted to a long wavelength side due to a temperature rise. The temperature changes of the respective LEDs 70 to 73 are caused by the increase or decrease of power to be supplied to the respective LEDs 70 to 73. That is, the wavelengths of lights to be emitted from the respective LEDs 70 to 73 are changed according to power to be supplied to the respective LEDs 70 to 73.

The light source optical system 74 combines the optical paths of the respective color lights of a red light RL, a green light GL, a blue light BL, and a violet light VL into one optical path, and condenses the respective color lights on the incident end of the light guide 45 of the endoscope 11. The light source optical system 74 includes: collimating lenses 75, 76, 77, and 78 that guide the respective color lights to the incident end of the light guide 45, respectively; dichroic mirrors 79, 80, and 81 that combine the optical paths of the respective color lights transmitted through the respective collimating lenses 75 to 78; and a condenser lens 82 that condenses the respective color lights on the incident end of the light guide 45.

The collimating lenses 75 to 78 transmit the respective color lights and change the respective color lights into lights substantially parallel to each other. Each of the dichroic mirrors 79 to 81 is an optical member where a dichroic filter having predetermined light transmission characteristics is formed on a transparent glass plate.

The green LED 71 is disposed at a position where the optical axis of the green LED 71 coincides with the optical axis of the light guide 45. Further, the red LED 70 and the green LED 71 are disposed so that the optical axes of the red LED 70 and the green LED 71 are orthogonal to each other. The dichroic mirror 79 is provided at a position where the optical axes of the red LED 70 and the green LED 71 are orthogonal to each other. Likewise, the blue LED 72 is also disposed so that the optical axis of the blue LED 72 is orthogonal to the optical axis of the green LED 71, and the dichroic mirror 80 is provided at a position where the optical axes of the blue LED 72 and the green LED 71 are orthogonal to each other. In addition, the blue LED 72 and the violet LED 73 are disposed so that the optical axes of the blue LED 72 and the violet LED 73 are orthogonal to each other, and the dichroic mirror 81 is provided at a position where the optical axes of the blue LED 72 and the violet LED 73 are orthogonal to each other.

The dichroic mirror 79 is disposed at an attitude where the dichroic mirror 79 is inclined with respect to the optical axis of the red LED 70 and the optical axis of the green LED 71 by an angle of 45°. The dichroic mirror 80 is disposed at an attitude where the dichroic mirror 80 is inclined with respect to the optical axis of the green LED 71 and the optical axis of the blue LED 72 by an angle of 45°. The dichroic mirror 81 is disposed at an attitude where the dichroic mirror 80 is inclined with respect to the optical axis of the blue LED 72 and the optical axis of the violet LED 73 by an angle of 45°.

The dichroic filter of the dichroic mirror 79 has, for example, characteristics that allow light in a red wavelength range having a wavelength of about 600 nm or more to be reflected and allow light in a blue wavelength range and a green wavelength range having a wavelength less than about 600 nm to be transmitted. For this reason, the dichroic mirror 79 reflects the red light RL emitted from the red LED 70 toward the condenser lens 82, and transmits the green light GL emitted from the green LED 71 toward the condenser lens 82. The optical paths of the green light GL and the red light RL are combined with each other by the action of the dichroic mirror 79.

The dichroic filter of the dichroic mirror 80 has, for example, characteristics that allow light in a blue wavelength range having a wavelength less than about 480 nm to be reflected and allow light in a green wavelength range and a red wavelength range having a wavelength of about 480 nm or more to be transmitted. For this reason, the dichroic mirror 80 transmits the green light GL, which is transmitted through the dichroic mirror 79, and the red light RL, which is reflected by the dichroic mirror 79, toward the condenser lens 82. Further, the dichroic mirror 80 reflects the blue light BL emitted from the blue LED 72 toward the condenser lens 82.

The dichroic filter of the dichroic mirror 81 has, for example, characteristics that allow light in a violet wavelength range having a wavelength less than about 430 nm to be reflected and allow light in a blue wavelength range, a green wavelength range, and a red wavelength range having a wavelength of 430 nm or more to be transmitted. For this reason, the dichroic mirror 81 transmits the blue light BL emitted from the blue LED 72 toward the condenser lens 82, and reflects the violet light VL emitted from the violet LED 73 toward the condenser lens 82. The optical paths of the blue light BL and the violet light VL are combined with each other by the action of the dichroic mirror 81. Since the dichroic mirror 80 has characteristics that allow light in a blue wavelength range having a wavelength less than about 480 nm to be reflected as described above, the violet light VL reflected by the dichroic mirror 81 is reflected toward the condenser lens 82 by the dichroic mirror 80. Accordingly, the optical paths of all of the red light RL, the green light GL, the blue light BL, and the violet light VL are combined.

Figure 6:
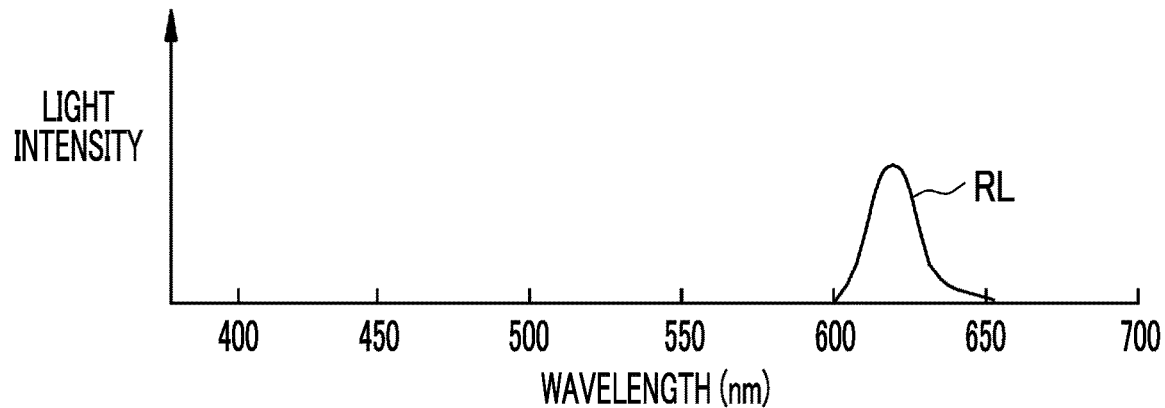
FIG. 6 is a graph showing the spectral characteristics of red light emitted from a red LED.
Figure 7:
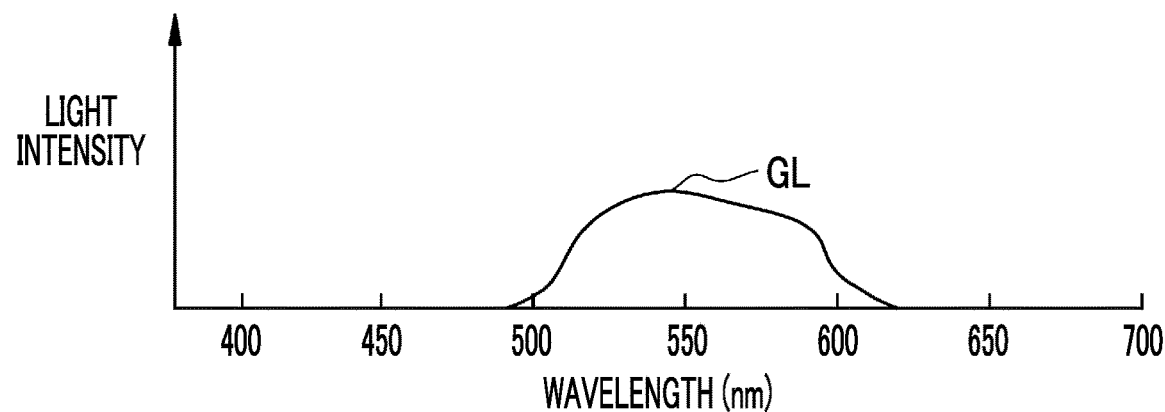
FIG. 7 is a graph showing the spectral characteristics of green light emitted from a green LED.

As shown in FIG. 6, the red LED 70 emits the red light RL, for example, including a wavelength component near the wavelength range of 600 nm to 650 nm that is a red wavelength range and having a central wavelength of 625±10 nm and a half-width of 20±10 nm. As shown in FIG. 7, the green LED 71 emits the green light GL, for example, including a wavelength component near the wavelength range of 480 nm to 600 nm that is a green wavelength range and having a central wavelength of 550±10 nm and a half-width of 100±10 nm.

Figure 8:
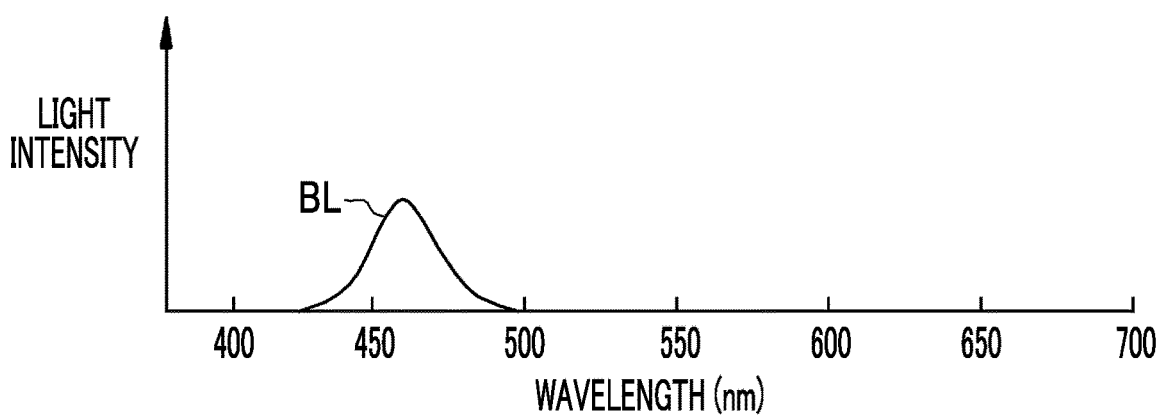
FIG. 8 is a graph showing the spectral characteristics of blue light emitted from a blue LED.
Figure 9:
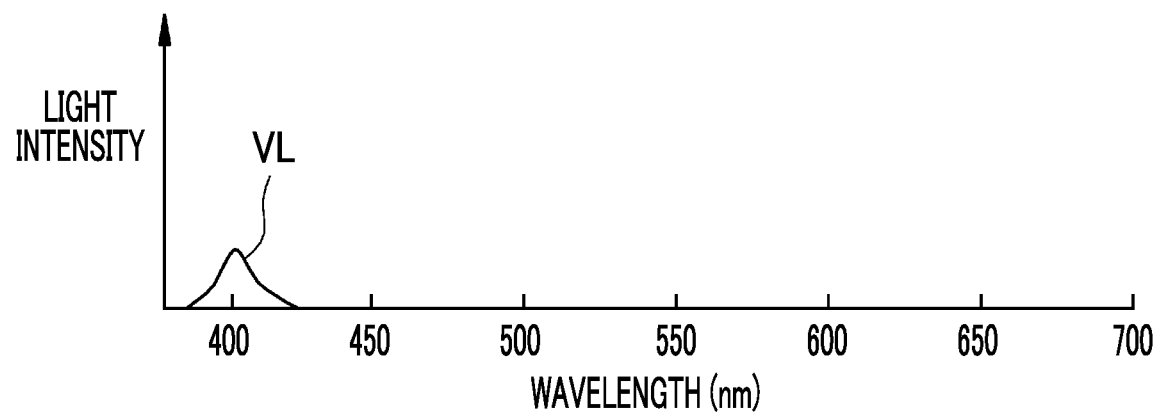
FIG. 9 is a graph showing the spectral characteristics of violet light emitted from a violet LED.

As shown in FIG. 8, the blue LED 72 emits the blue light BL, for example, including a wavelength component near the wavelength range of 420 nm to 500 nm that is a blue wavelength range and having a central wavelength of 460±10 nm and a half-width of 25±10 nm. As shown in FIG. 9, the violet LED 73 emits the violet light VL, for example, including a wavelength component near the wavelength range of 380 nm to 420 nm that is a violet wavelength range and having a central wavelength of 405±10 nm and a half-width of 20±10 nm. A central wavelength means a wavelength corresponding to the center of the width of the spectral characteristics (also referred to as a light emission spectrum) of each color light, and a half-width is the range of a wavelength that represents the half of the peak of the spectral characteristics of each color light.

Figure 10:
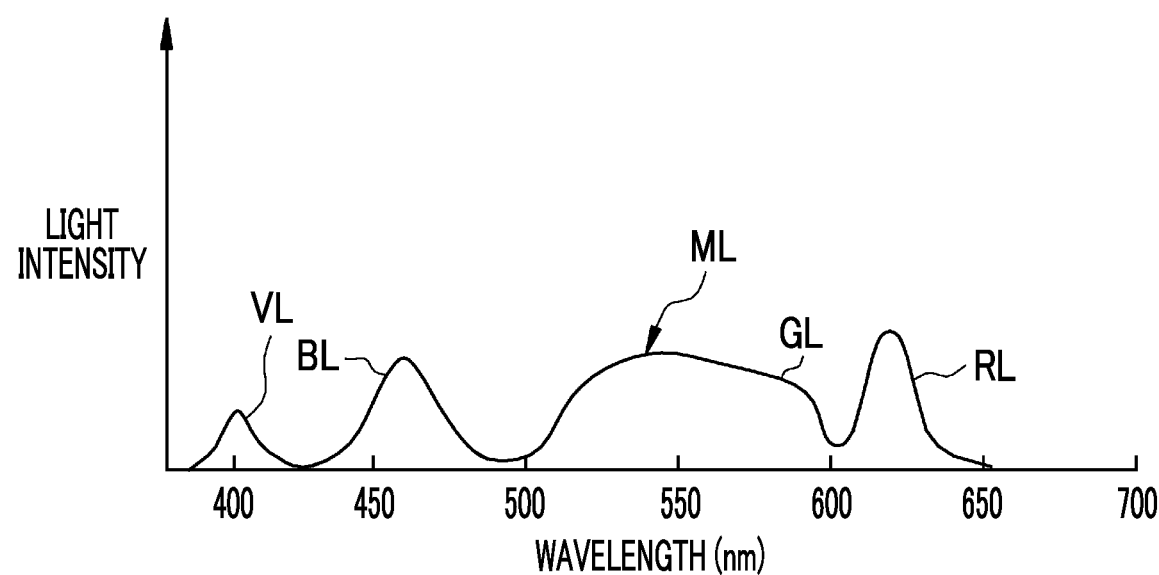
FIG. 10 is a graph showing the spectral characteristics of mixed light that is formed of red light, green light, blue light, and violet light.

FIG. 10 shows the spectral characteristics of mixed light ML of the red light RL, the green light GL, the blue light BL, and the violet light VL of which the optical paths are combined by the light source optical system 74. The mixed light ML is used as illumination light with which the object to be observed is to be illuminated. To maintain the same color rendering properties as those of white light emitted from a xenon lamp, the mixed light ML is formed so that a wavelength range where a light intensity component is not present is not formed.

Figure 11:
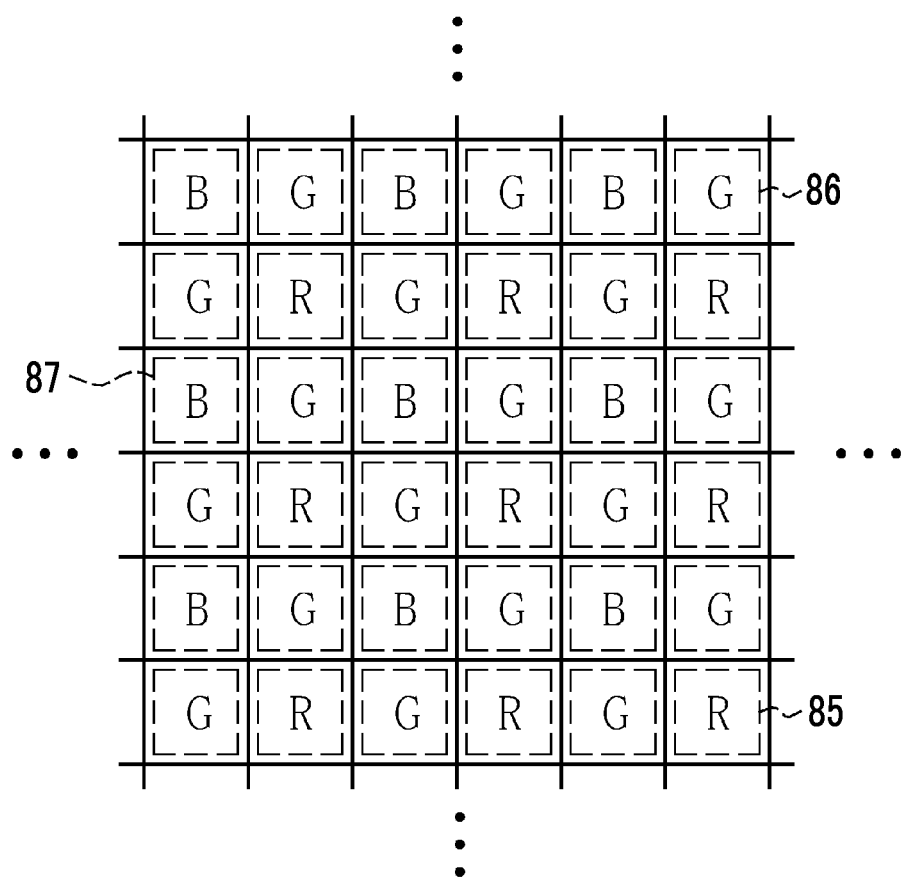
FIG. 11 is a diagram showing the array of color filters.

In FIG. 11, color filters having the respective colors of a red, a green, and a blue, (red filters 85, green filters 86, and blue filters 87) are provided on the image pickup surface 46A of the image pickup element 46. These color filters 85 to 87 form so-called Bayer array, and the green filters 86 are arranged on every other pixel in a checker pattern and the red filters 85 and the blue filters 87 are arranged on the other pixels in a square lattice pattern. In the following description, the pixel to which the red filter 85 is assigned will be referred to as an R pixel, the pixel to which the green filter 86 is assigned will be referred to as a G pixel, and the pixel to which the blue filter 87 is assigned will be referred to as a B pixel.

Figure 12:
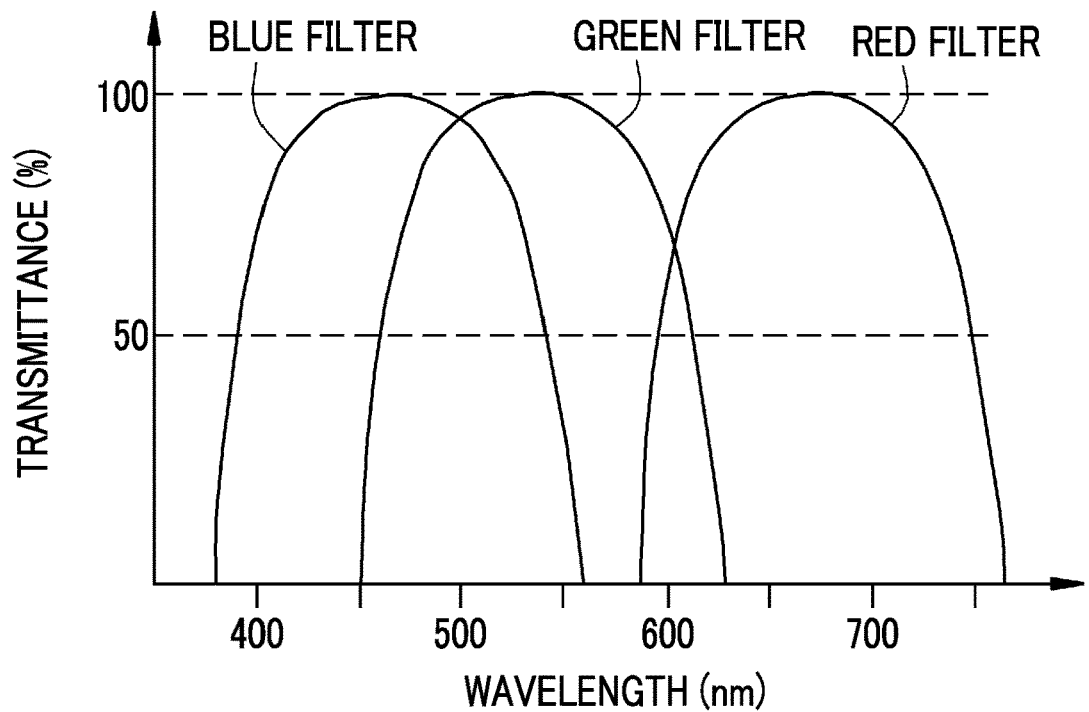
FIG. 12 is a graph showing the spectral characteristics of the color filters.

FIG. 12 shows the spectral characteristics (referred to as spectral transmission characteristics) of the respective color filters 85 to 87. According to the spectral characteristics, the R pixel to which the red filter 85 is assigned responds to light in a wavelength range of about 580 nm to 800 nm and the G pixel to which the green filter 86 is assigned responds to light in a wavelength range of about 450 nm to 630 nm. Further, the B pixel to which the blue filter 87 is assigned responds to light in a wavelength range of about 380 nm to 560 nm. Among the red light RL, the green light GL, the blue light BL, and the violet light VL, which form the mixed light ML, reflected light corresponding to the red light RL is mainly received by the R pixels, reflected light corresponding to the green light GL is mainly received by the G pixels, and reflected light corresponding to the blue light BL and the violet light VL is mainly received by the B pixels.

Figure 13:
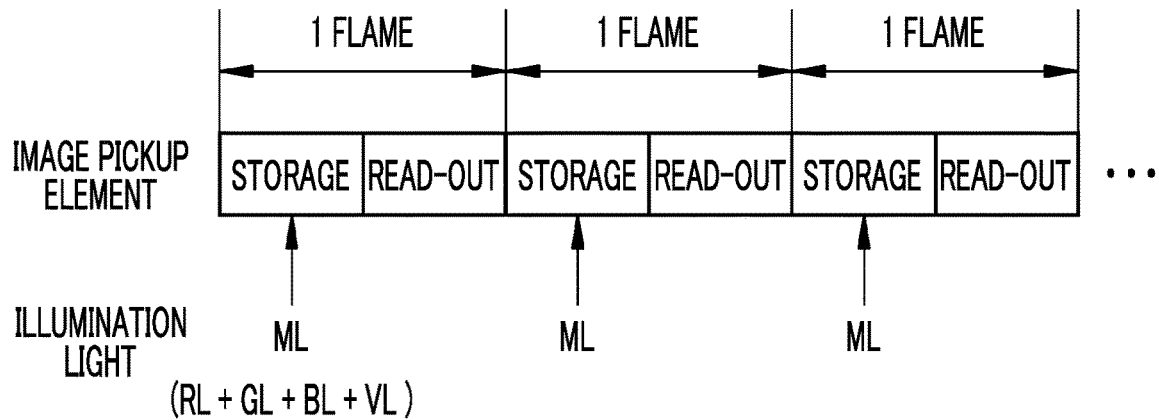
FIG. 13 is a diagram showing the irradiation timing of illumination light and the operation timing of an image pickup element.

In FIG. 13, the image pickup element 46 performs a storage operation for storing signal charges in pixels and a read-out operation for reading out the stored signal charges, during periods in which image pickup signals of one frame are acquired. The respective LEDs 70 to 73 are turned on in accordance with the timing of the storage operation of the image pickup element 46. Accordingly, the object to be observed is irradiated with the mixed light ML (RL+GL+BL+VL) as illumination light and the reflected light of the mixed light ML is incident on the image pickup element 46. The image pickup element 46 performs the color separation of the reflected light of the mixed light ML by the respective color filters 85 to 87. That is, reflected light corresponding to the red light RL is received by the R pixels, reflected light corresponding to the green light GL is received by the G pixels, and reflected light corresponding to the blue light BL and the violet light VL is received by the B pixels. The image pickup element 46 sequentially outputs the image pickup signals of one frame according to a frame rate in accordance with a timing when the signal charges are read out.

All the respective LEDs 70 to 73 are turned on regardless of each of the normal observation mode and the special observation mode. However, a ratio of the amount of the green light GL having relatively high spectral luminous efficiency is set high in the normal observation mode for the observation of overall properties of the object to be observed. Accordingly, since the object to be observed is irradiated with pseudo white light of which the amount is sufficient in the normal observation mode, a bright image can be obtained. On the other hand, a ratio of the amount of the violet light VL, of which the absorption coefficient in a superficial blood vessel is high, is set high in the special observation mode for the emphasis and observation of the superficial blood vessel of the object to be observed. Further, a ratio of the amount of the green light GL, of which the absorption coefficient in an intermediate blood vessel obstructive to the observation of the superficial blood vessel is high, is set low. Accordingly, an image in which the structure of the superficial blood vessel closely related to a lesion, such as a tumor, is emphasized can be obtained in the special observation mode. Furthermore, a ratio of the amount of the green light GL may be set high as with that of the violet light VL in the special observation mode to obtain an image in which the visualization and brightness of the structure of the superficial blood vessel are compatible with each other.

Figure 14:
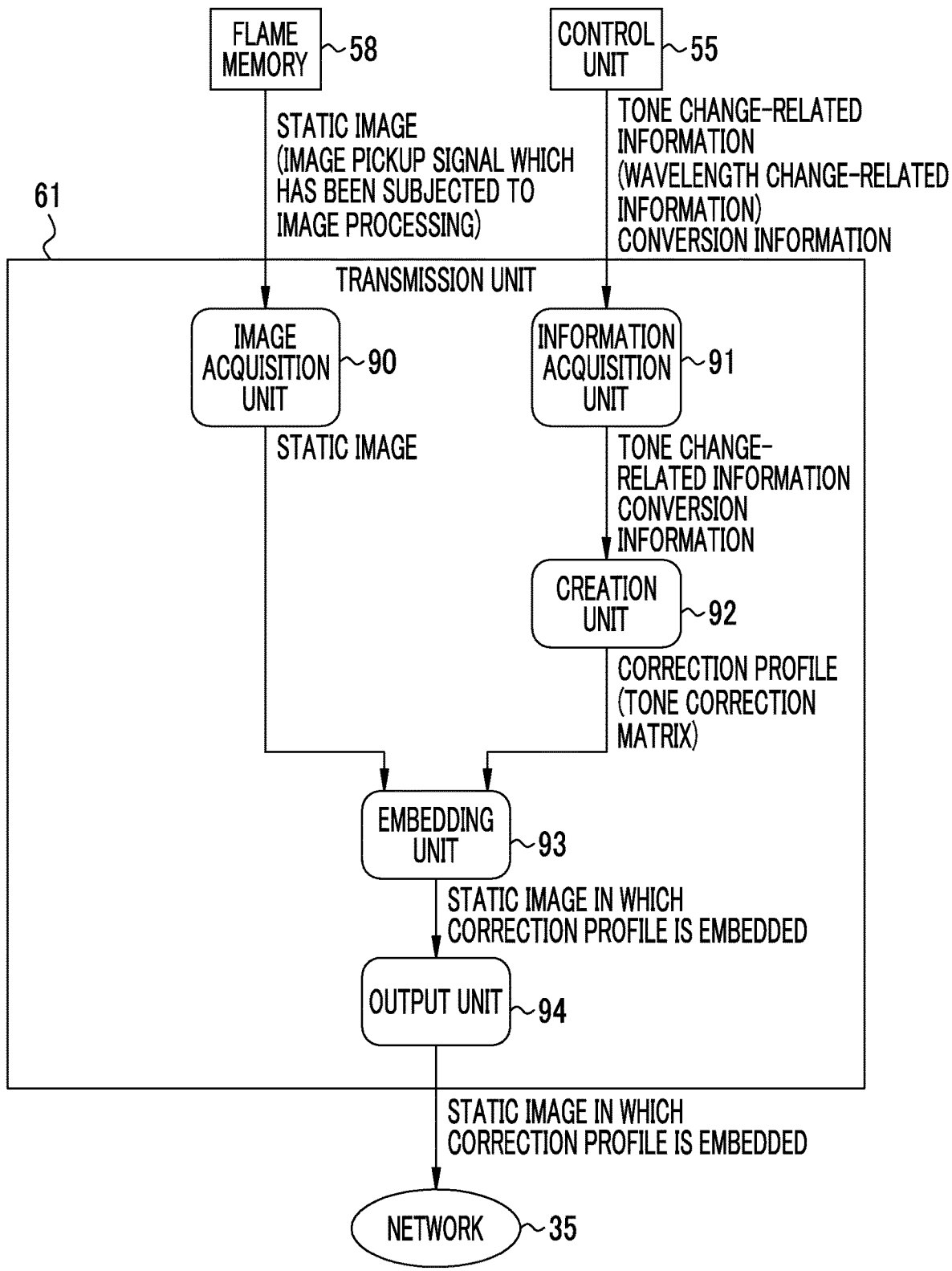
FIG. 14 is a block diagram of a transmission unit.

In FIG. 14, the transmission unit 61 comprises an image acquisition unit 90, an information acquisition unit 91, a creation unit 92, an embedding unit 93, and an output unit 94.

The image acquisition unit 90 reads out the image pickup signals, of which the rewriting is temporarily stopped by a recording instruction signal and which have been subjected to image processing, from the frame memory 58. That is, the image acquisition unit 90 acquires the static image of the object to be observed that is picked up according to an operator's instruction for operation. The image acquisition unit 90 outputs the acquired static image to the embedding unit 93.

The information acquisition unit 91 acquires tone change-related information and conversion information from the control unit 55. The tone change-related information is information about a change in the tone of the static image. In this embodiment, the tone change-related information is wavelength change-related information about a change in the wavelength of illumination light. The conversion information is information that is used to convert the tone change-related information into a correction profile for correcting a change in the tone of the static image. The information acquisition unit 91 outputs the acquired tone change-related information and the acquired conversion information to the creation unit 92.

The creation unit 92 creates a correction profile corresponding to the tone change-related information and the conversion information that are output from the information acquisition unit 91. The correction profile is used to correct the tone of the static image to reference tone in a case where the tone of the static image deviates from the reference tone. The creation unit 92 outputs the created correction profile to the embedding unit 93.

The embedding unit 93 embeds the correction profile, which is output from the creation unit 92, in the static image that is output from the image acquisition unit 90. Embedding the correction profile in the static image specifically refers to as recording the correction profile as the supplementary information of the static image in association with the static image. The embedding unit 93 outputs the static image, in which the correction profile is embedded, to the output unit 94.

The output unit 94 outputs the static image, in which the correction profile output from the embedding unit 93 is embedded, to a designated external transmission destination. The external transmission destination is specifically the image storage server 36 that is connected through the network 35. The image storage server 36, which is the transmission destination, is designated in advance through the input unit 15 by an operator.

Figure 15A:
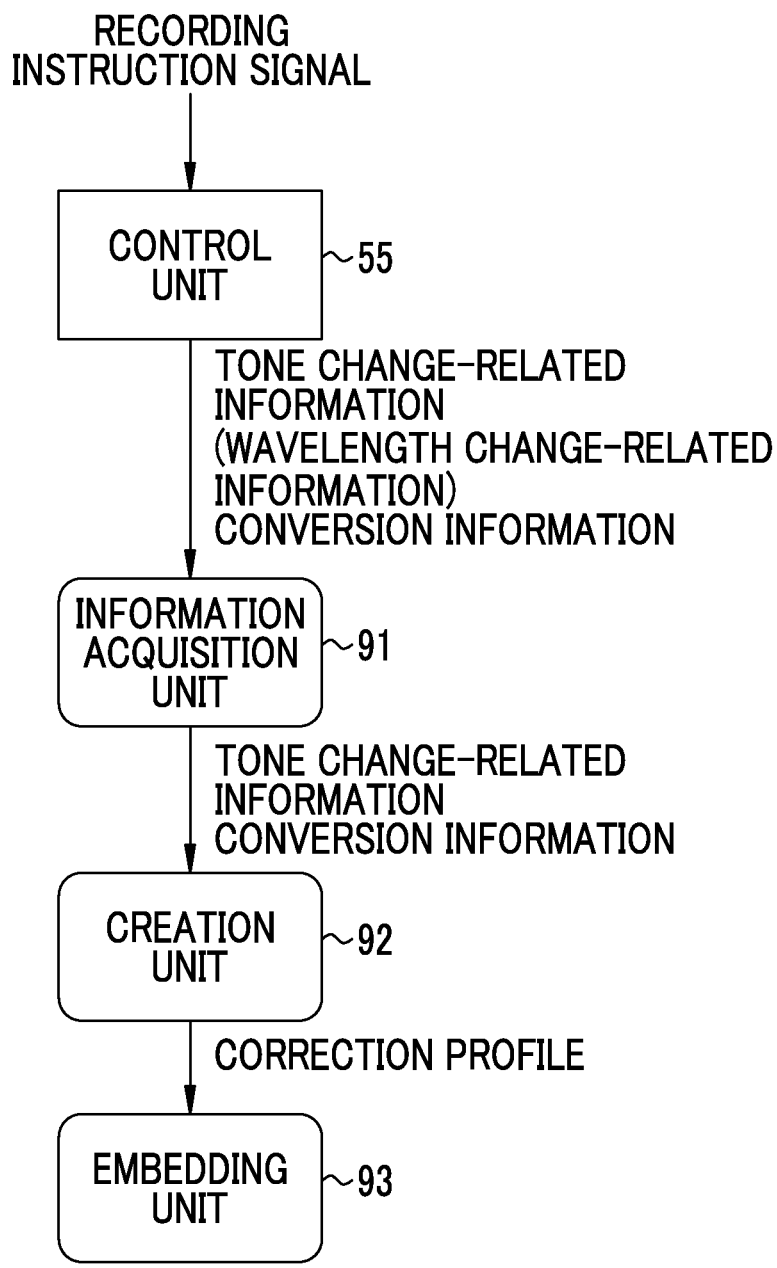
FIG. 15A is a diagram showing an aspect where tone change-related information is acquired only in a case where an operator gives an instruction for operation, and shows an aspect where tone change-related information and conversion information are output to an information acquisition unit from a control unit in a case where a recording instruction signal is input.
Figure 15B:
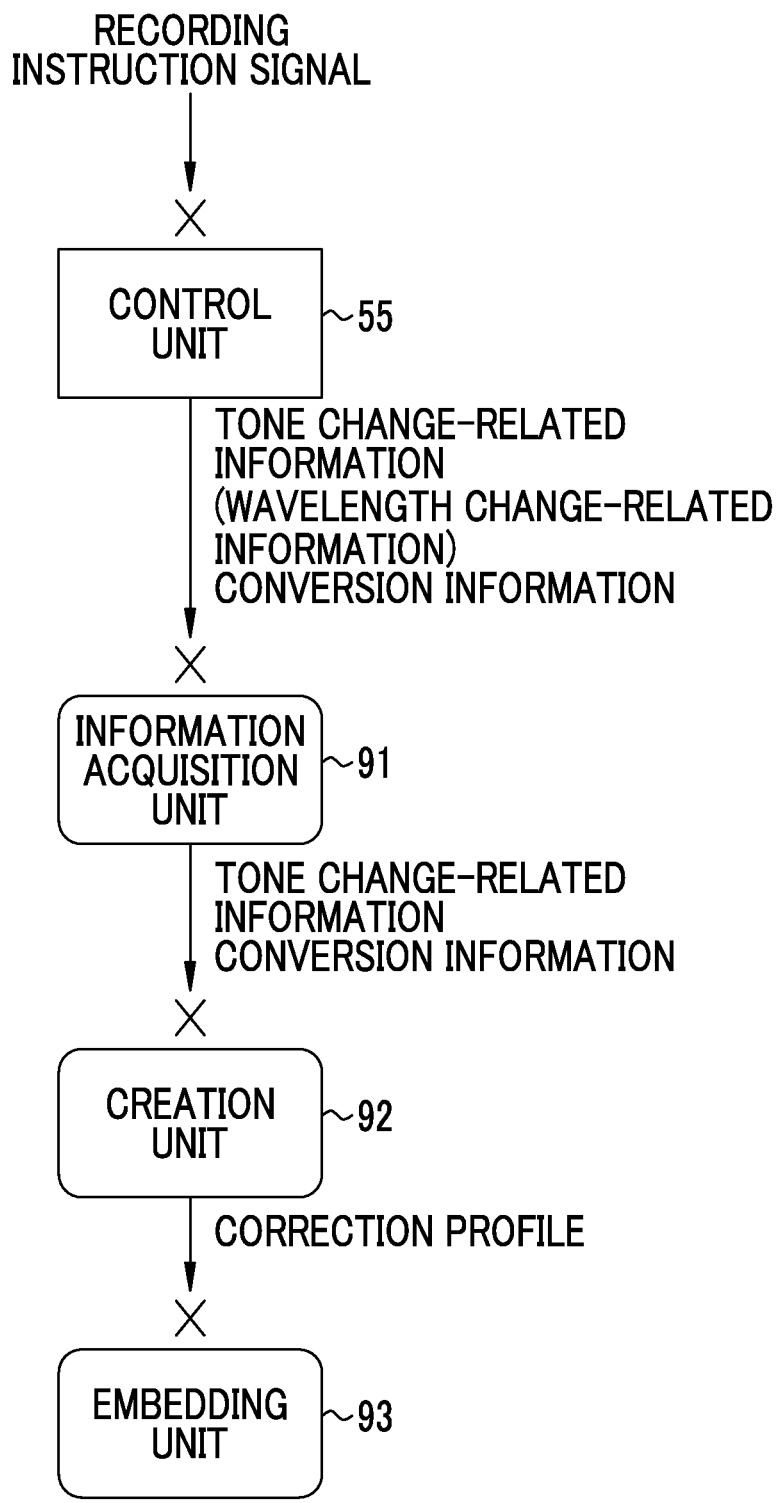
FIG. 15B is a diagram showing an aspect where tone change-related information is acquired only in a case where an operator gives an instruction for operation, and shows an aspect where tone change-related information and conversion information are not output to the information acquisition unit from the control unit in a case where a recording instruction signal is not input.

As shown in FIG. 15A, the control unit 55 outputs the tone change-related information and the conversion information to the information acquisition unit 91 in a case where a recording instruction signal is input to the control unit 55 from the signal transmission/reception unit 56. In contrast, as shown in FIG. 15B, the control unit 55 does not output the tone change-related information and the conversion information to the information acquisition unit 91 in a case where a recording instruction signal is not input to the control unit 55 from the signal transmission/reception unit 56. That is, the tone change-related information is acquired by the information acquisition unit 91 only in a case where an operator gives an instruction for operation.

Since the tone change-related information and the like are not output to the creation unit 92 from the information acquisition unit 91 in the case of FIG. 15B, a correction profile is not created naturally by the creation unit 92. That is, a correction profile is not created in a case where an instruction for operation is not given, and is created only in a case where an instruction for operation is given.

Figure 16:
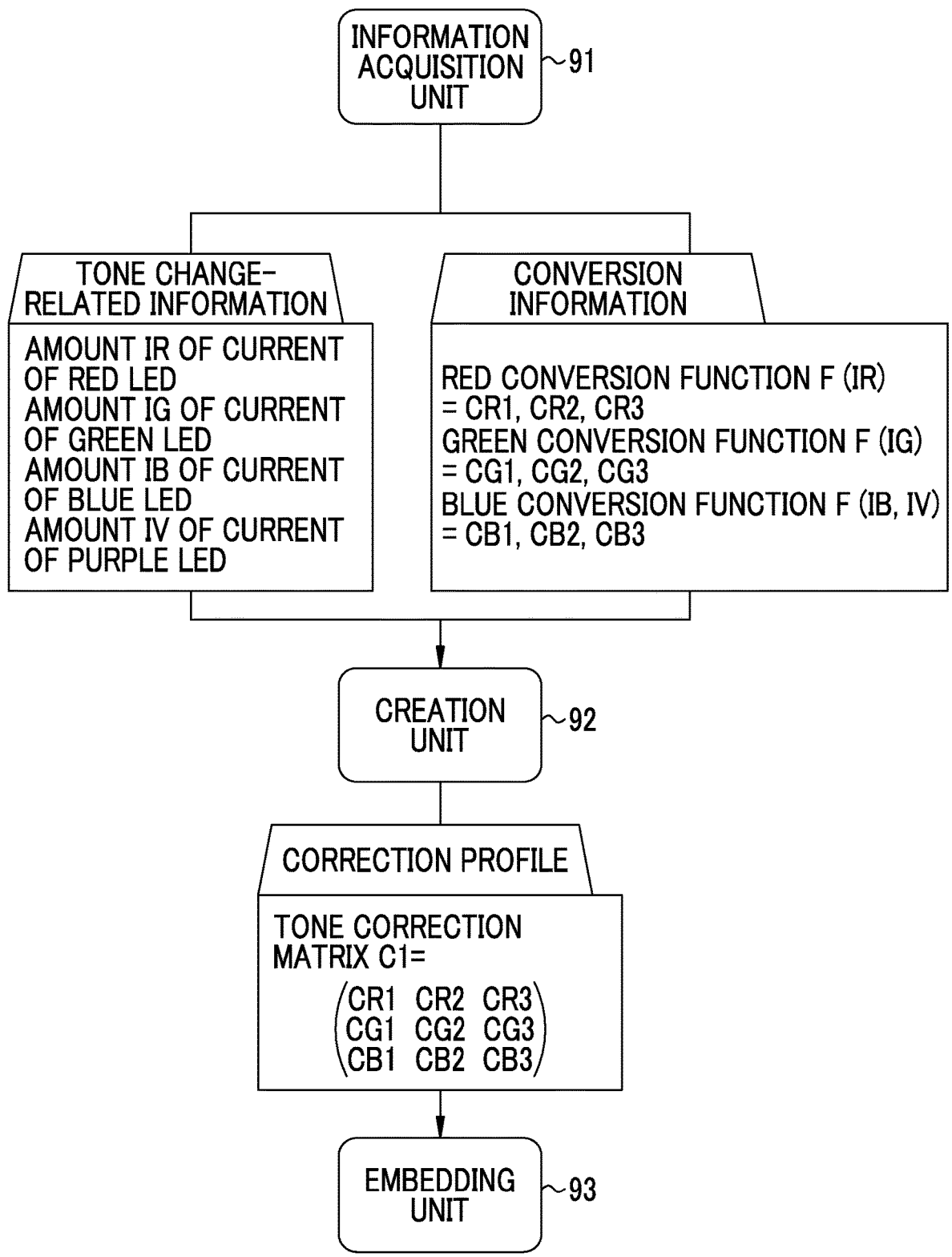
FIG. 16 is a diagram showing an aspect where a correction profile according to tone change-related information and conversion information is created.

As shown in FIG. 16, the tone change-related information of this embodiment is the amounts IR to IV of current of the respective LEDs 70 to 73. Since the wavelengths of lights emitted from the respective LEDs 70 to 73 are changed according to the amounts IR to IV of current as described above, the amounts IR to IV of current correspond to the wavelength change-related information.

The amounts IR to IV of current are represented by exposure control signals. The control unit 55 outputs the amounts IR to IV of current, which are represented by exposure control signals lately output to the light source control unit 66, to the information acquisition unit 91 as the tone change-related information in a case where a recording instruction signal is input to the control unit 55 from the signal transmission/reception unit 56.

The conversion information is a red conversion function F(IR), a green conversion function F(IG), and a blue conversion function F(IB, IV). The red conversion function F(IR) is a function for obtaining matrix coefficients CR1, CR2, and CR3; the green conversion function F(IG) is a function for obtaining matrix coefficients CG1, CG2, and CG3; and the blue conversion function F(IB, IV) is a function for obtaining matrix coefficients CB1, CB2, and CB3. The red conversion function F(IR) has the amount IR of current of the red LED 70 as a variable, the green conversion function F(IG) has the amount IG of current of the green LED 71 as a variable, and the blue conversion function F(IB, IV) has the amount IB of current of the blue LED 72 and the amount IV of current of the violet LED 73 as variables.

The creation unit 92 creates a tone correction matrix C1 by substituting each of the amounts of current of the tone change-related information into each conversion function of the conversion information and making a calculation. More specifically, the red matrix coefficients CR1 to CR3 are obtained from the red conversion function F(IR), the green matrix coefficients CG1 to CG3 are obtained from the green conversion function F(IG), and the blue matrix coefficients CB1 to CB3 are obtained from the blue conversion function F(IB, IV). Then, a matrix of 3*3 in which these matrix coefficients CR1 to CR3, CG1 to CG3, and CB1 to CB3 are arranged is created as the tone correction matrix C1. The tone correction matrix C1 can be embedded in a standard color profile, for example, an international color consortium (ICC) profile. The creation unit 92 outputs the created tone correction matrix C1 to the embedding unit 93 as the correction profile.

The respective conversion functions of the conversion information are stored in a storage unit (for example, an ROM 134 or the like shown in FIG. 22) of the light source device 13 in advance. In a case where the light source device 13 is connected to the processor device 12, the respective conversion functions are transmitted to the processor device 12 from the light source device 13 and are written in, for example, an ROM (not shown) of the control unit 55.

Not the conversion functions but a data table in which the matrix coefficients corresponding to the amounts IR to IV of current of the respective LEDs 70 to 73 are registered may be used. Further, the wavelength change-related information is not limited to the amounts IR to IV of current of the respective LEDs 70 to 73 and may be the peak wavelengths of the respective color lights or may be the amounts of shift of the peak wavelengths of the respective color lights from a reference peak wavelength. Alternatively, the amounts of the respective color lights may be used as the wavelength change-related information.

Figure 17:
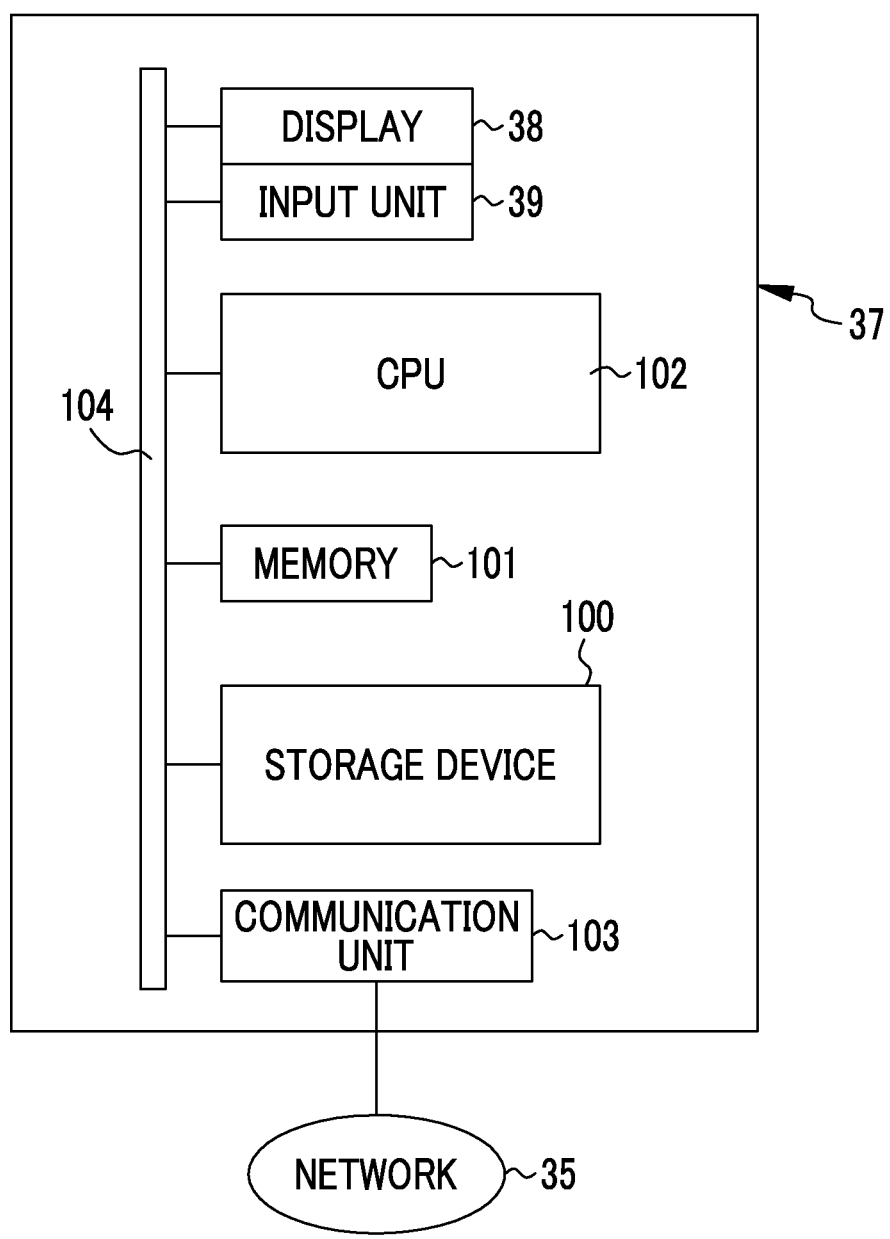
FIG. 17 is a block diagram of a computer forming the image display device.

In FIG. 17, the computer forming the image display device 37 comprises a storage device 100, a memory 101, a CPU 102, and a communication unit 103 in addition to the display 38 and the input unit 39 having been described above. These components are connected to each other through a data bus 104.

The storage device 100 is a hard disk drive, which is built in the computer forming the image display device 37 or is connected the computer through a cable or a network, or a disk array in which a plurality of hard disk drives are arranged. A control program, such as an operating system, various application programs (hereinafter, abbreviated as APs), various data appendant to these programs, and the like are stored in the storage device 100.

The memory 101 is a work memory that is used in a case where the CPU 102 performs processing. The CPU 102 loads the programs, which are stored in the storage device 100, into the memory 101 and generally controls the respective parts of the computer by performing processing according to the programs.

The communication unit 103 is a network interface that controls the transmission of various kinds of information to/from the image storage server 36 and the like through the network 35. The communication unit 103 transmits a delivery request for a static image to the image storage server 36, and receives a static image from the image storage server 36.

Figure 18:
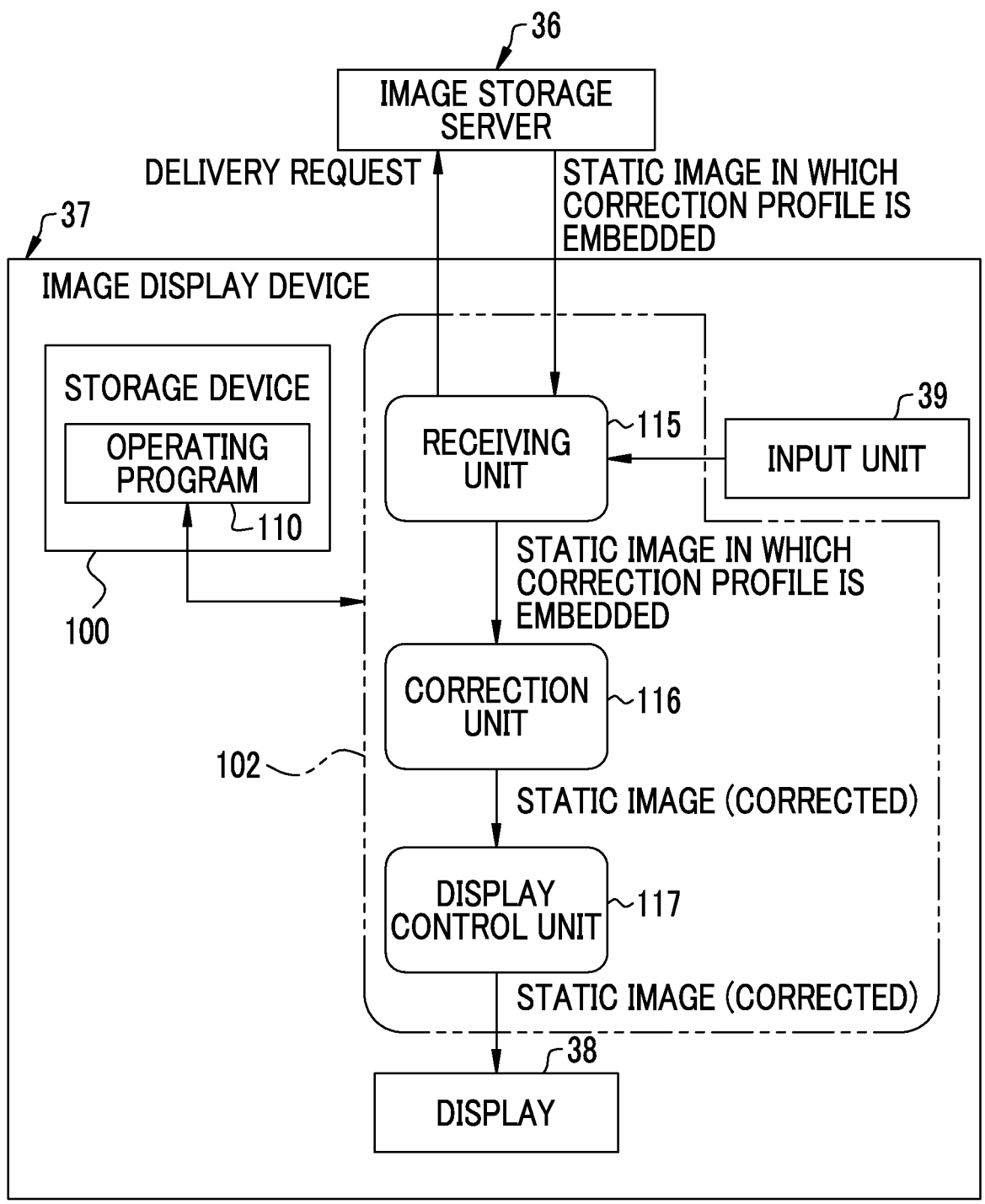
FIG. 18 is a block diagram of a CPU of the computer forming the image display device.

In FIG. 18, an operating program 110 is stored in the storage device 100 of the image display device 37 as an AP. The operating program 110 is an AP that causes the computer to function as the image display device 37.

In a case where the operating program 110 is started, the CPU 102 of the image display device 37 functions as a receiving unit 115, a correction unit 116, and a display control unit 117 in cooperation with the memory 101 and the like.

The receiving unit 115 issues a delivery request for a static image including search keys (the order identification data (ID) of endoscopy, a patient name, a patient name ID, an endoscopy date, an operator name, and the like), which are input from the input unit 39, to the image storage server 36. Further, the receiving unit 115 has a reception function to receive a static image that is transmitted from the image storage server 36 according to a delivery request. This static image is a static image in which the correction profile is embedded by the embedding unit 93 of the transmission unit 61 of the processor device 12. The receiving unit 115 outputs the received static image to the correction unit 116.

The correction unit 116 has a correction function to correct the static image by using the correction profile that is embedded in the static image. Specifically, in a case where an uncorrected static image is denoted by BI, the correction unit 116 multiplies the tone correction matrix C1 and the static image BI together to calculate a corrected static image AI1 as shown in Equation (1).

$$AI1 = C1 \cdot BI \quad (1)$$

Here, in a case where image pickup signals of the corrected static image AI1 corresponding to the respective colors of a red, a green, and a blue are denoted by AIR1, AIG1, and AIB1 and image pickup signals of the uncorrected static image BI corresponding to the respective colors of a red, a green, and a blue are denoted by BIR, BIG, and BIB, Equation (1) is rewritten as Equation (2).

$$\begin{pmatrix} AIR1 \\ AIG1 \\ AIB1 \end{pmatrix} = \begin{pmatrix} CR1 & CR2 & CR3 \\ CG1 & CG2 & CG3 \\ CB1 & CB2 & CB3 \end{pmatrix} \begin{pmatrix} BIR \\ BIG \\ BIB \end{pmatrix} \quad (2)$$

In this way, the matrix coefficients CR1 to CR3, CG1 to CG3, and CB1 to CB3 are multiplied by the image pickup signals BIR, BIG, and BIB corresponding to the respective colors of a red, a green, and a blue, respectively.

Since the above-mentioned correction is performed on the static image BI, the static image AI1 of which the tone is corrected to a reference tone can be obtained. The correction unit 116 outputs the corrected static image AI1 to the display control unit 117.

The display control unit 117 has a display control function to control the display of the corrected static image AI1 on the display 38.

Figure 19:
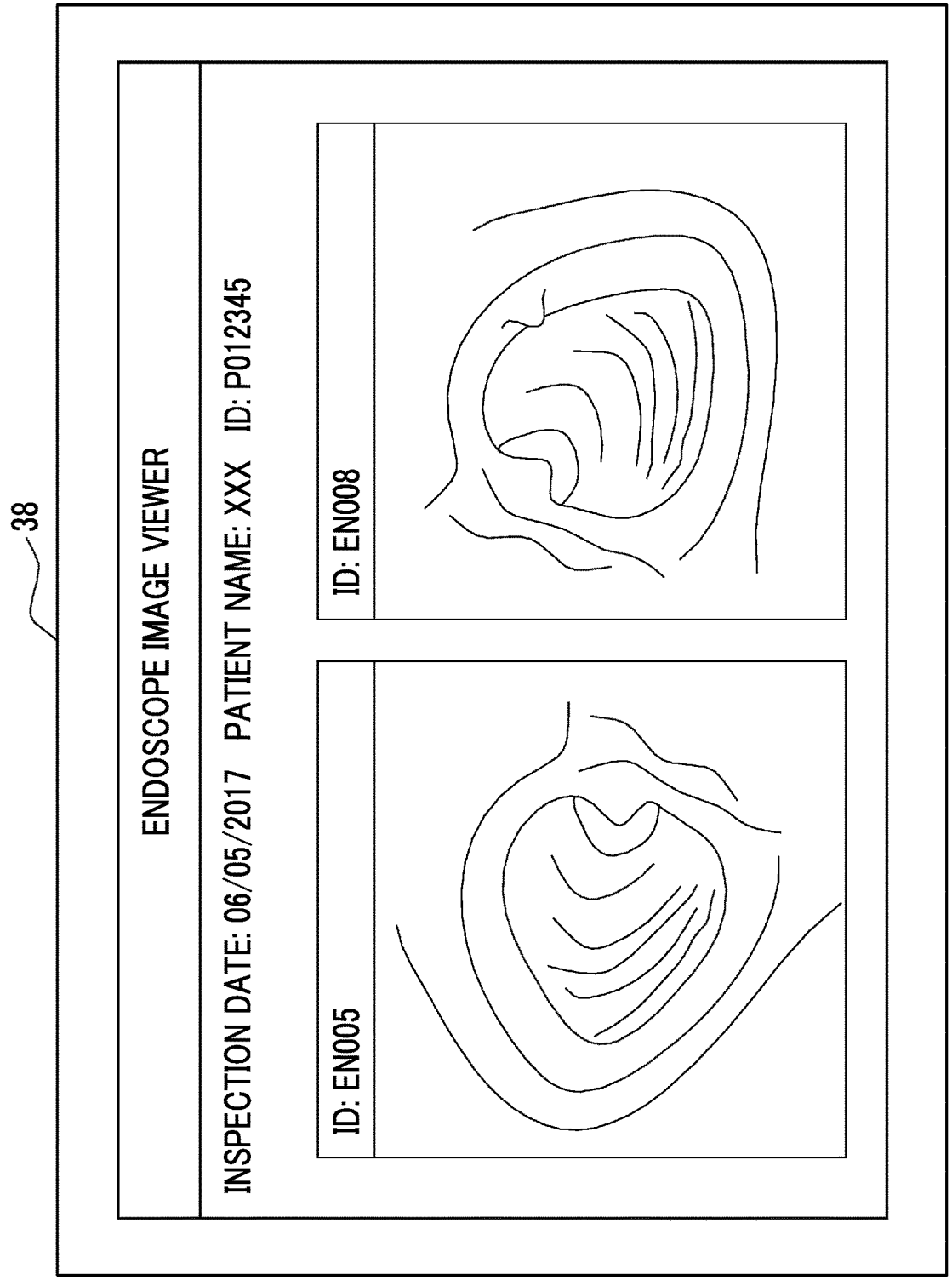
FIG. 19 is a diagram showing an aspect where a plurality of static images are arranged and displayed.

As shown in FIG. 19, the display control unit 117 has a function to arrange and display a plurality of static images on the display 38. FIG. 19 shows an example where two static images (ID: "EN005" and "EN008") obtained from single endoscopy performed for the same patient ("xxx" having ID of "P012345") at the same date ("2017/06/05") are arranged and displayed. The plurality of static images, which are arranged and displayed, are not limited to the example shown in FIG. 19, and may be a plurality of static images that are obtained from a combination of the other endoscope 11 and the other light source device 13.

Next, the action of the above-mentioned configuration will be described with reference to flowcharts of FIGS. 20 and 21. In a case where endoscopy is to be performed in the medical facility, the endoscope 11 is connected to the processor device 12 and the light source device 13 and power is supplied to the processor device 12 and the light source device 13 to start the endoscope system 10. Then, the insertion part 16 of the endoscope 11 is inserted into an object to be examined to start the observation of the inside of the object to be examined.

In the light source device 13, the amounts IR to IV of current to be supplied to the respective LEDs 70 to 73 are set to the respective LEDs 70 to 73 from the light source control unit 66. Accordingly, the respective LEDs 70 to 73 start to be turned on. Further, the amounts of the respective color lights are controlled by the light source control unit 66 to maintain target spectral characteristics.

The optical paths of the respective color lights RL to VL emitted from the respective LEDs 70 to 73 are combined by the light source optical system 74, so that the respective color lights RL to VL form the mixed light ML. The mixed light ML is guided to the illumination windows 31 by the light guide 45, and the object to be observed is irradiated with the mixed light ML as illumination light from the illumination windows 31. The reflected light of the mixed light ML, which is reflected by the object to be observed, is incident on the image pickup element 46 from the observation window 30. In the image pickup element 46, the reflected light is subjected to color separation by the color filters 85 to 87 having the respective colors. As a result, image pickup signals corresponding to the respective colors of a red, a green, and a blue are output from the image pickup element 46. These image pickup signals are output to the processor device 12 from the signal transmission/reception unit 48.

In the processor device 12, the image pickup signals are received by the signal transmission/reception unit 56 and are output to the DSP 57. In the DSP 57, the image pickup signals are subjected to various kinds of processing. After that, the image pickup signals are written in the frame memory 58 by the DSP 57.

In the DSP 57, exposure values are calculated on the basis of the image pickup signals. Exposure control signals corresponding to the exposure values are generated by the control unit 55 and are transmitted to the light source control unit 66. The respective LEDs 70 to 73 are driven by the amounts IR to IV of current that are represented by the exposure control signals. Accordingly, the amounts of the red light RL, the green light GL, the blue light BL, and the violet light VL, which are emitted from the respective LEDs 70 to 73 and form the mixed light ML serving as illumination light, can be kept at constant intensities and constant ratios suitable for observation.

After the image pickup signals of the frame memory 58 are read out and are subjected to various kinds of image processing by the image processing unit 59, the image pickup signals are output to the monitor 14 through the display control unit 60 as the image of the object to be observed. The display of the image is updated according to the frame rate of the image pickup element 46.

An operator observes the video of the object to be observed displayed on the monitor 14. In a case where a lesion, such as a tumor, is found on the object to be observed, the operator performs an operation for pressing the release button 23 to intend recording the static image of the object to be observed. Accordingly, a recording instruction signal is generated from the release button 23. The recording instruction signal is transmitted to the signal transmission/reception unit 56 from the signal transmission/reception unit 48, and is input to the control unit 55 from the signal transmission/reception unit 56.

Figure 20:
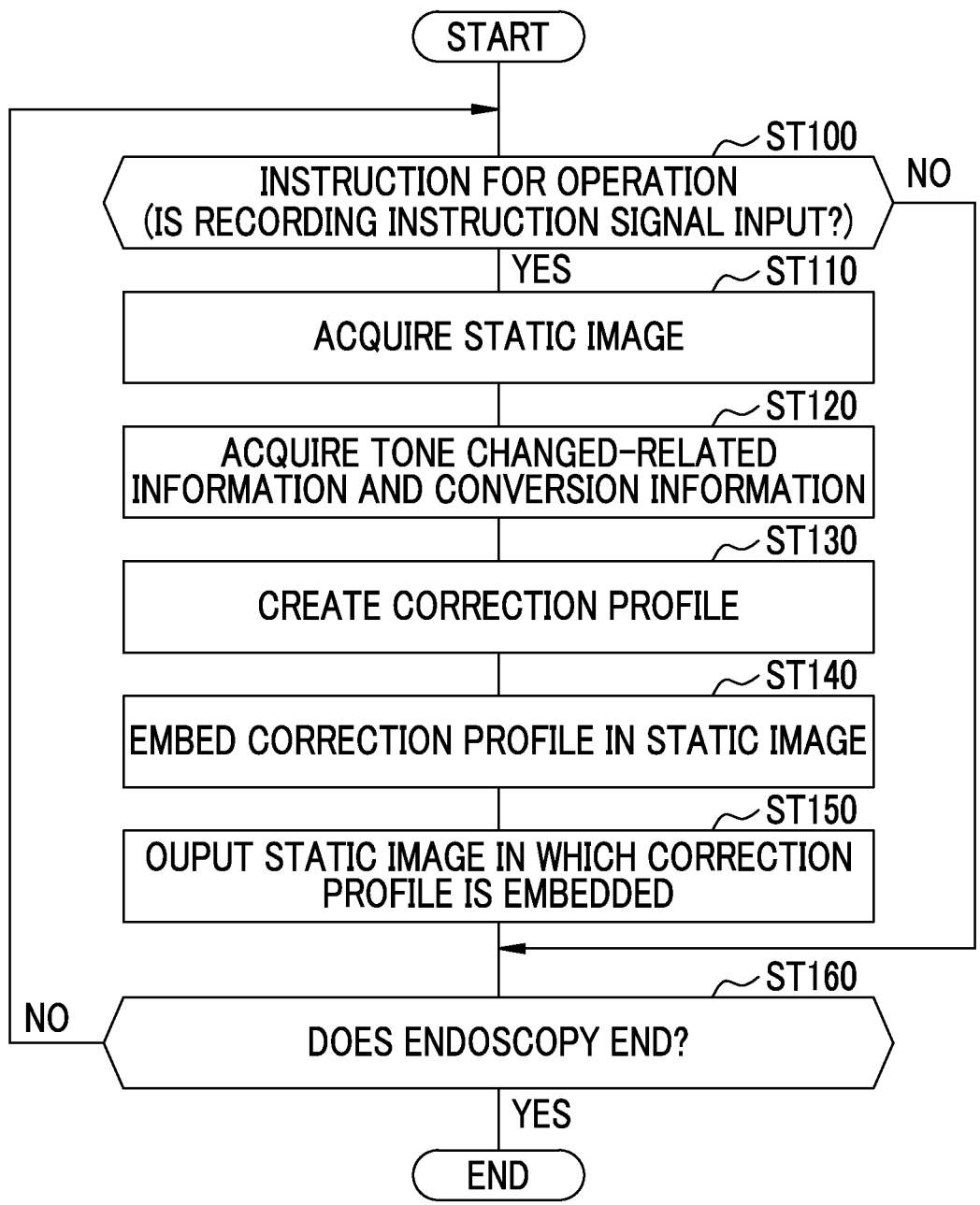
FIG. 20 is a flowchart showing the procedure of processing of a processor device.

In FIG. 20, in a case where a recording instruction signal is input to the control unit 55 (YES in Step ST100), the rewriting of the image pickup signals in the frame memory 58 by the DSP 57 is temporarily stopped by the control unit 55.

Then, the image pickup signals, of which the rewriting is temporarily stopped and have been subjected to image processing, are read out from the frame memory 58 by the image acquisition unit 90. Accordingly, the static image of the object to be observed, which is picked up according to an operator's instruction for operation, is acquired (Step ST110, image acquisition step). The static image is output to the embedding unit 93 from the image acquisition unit 90.

In parallel with the image acquisition step of Step ST110, the tone change-related information and the conversion information output from the control unit 55 are acquired by the information acquisition unit 91 as shown in FIG. 15A (Step ST120). The tone change-related information and the conversion information are output to the creation unit 92 from the information acquisition unit 91.

As shown in FIG. 16, a correction profile is created in the creation unit 92 according to the tone change-related information and the conversion information that are output from the information acquisition unit 91 (Step ST130). The correction profile is output to the embedding unit 93 from the creation unit 92.

In the embedding unit 93, the correction profile output from the creation unit 92 is embedded in the static image output from the image acquisition unit 90 (Step ST140, embedding step). The static image in which the correction profile is embedded is output to the image storage server 36 by the output unit 94 (Step ST150, output step). These series of processing are repeatedly continued until endoscopy ends (YES in Step ST160).

A medical doctor of the diagnosis and treatment department starts the operating program 110 in the image display device 37 to observe the static image of endoscopy for which the medical doctor has given an order. Accordingly, the CPU 102 of the computer forming the image display device 37 functions as the receiving unit 115, the correction unit 116, and the display control unit 117 as shown in FIG. 18.

Figure 21:
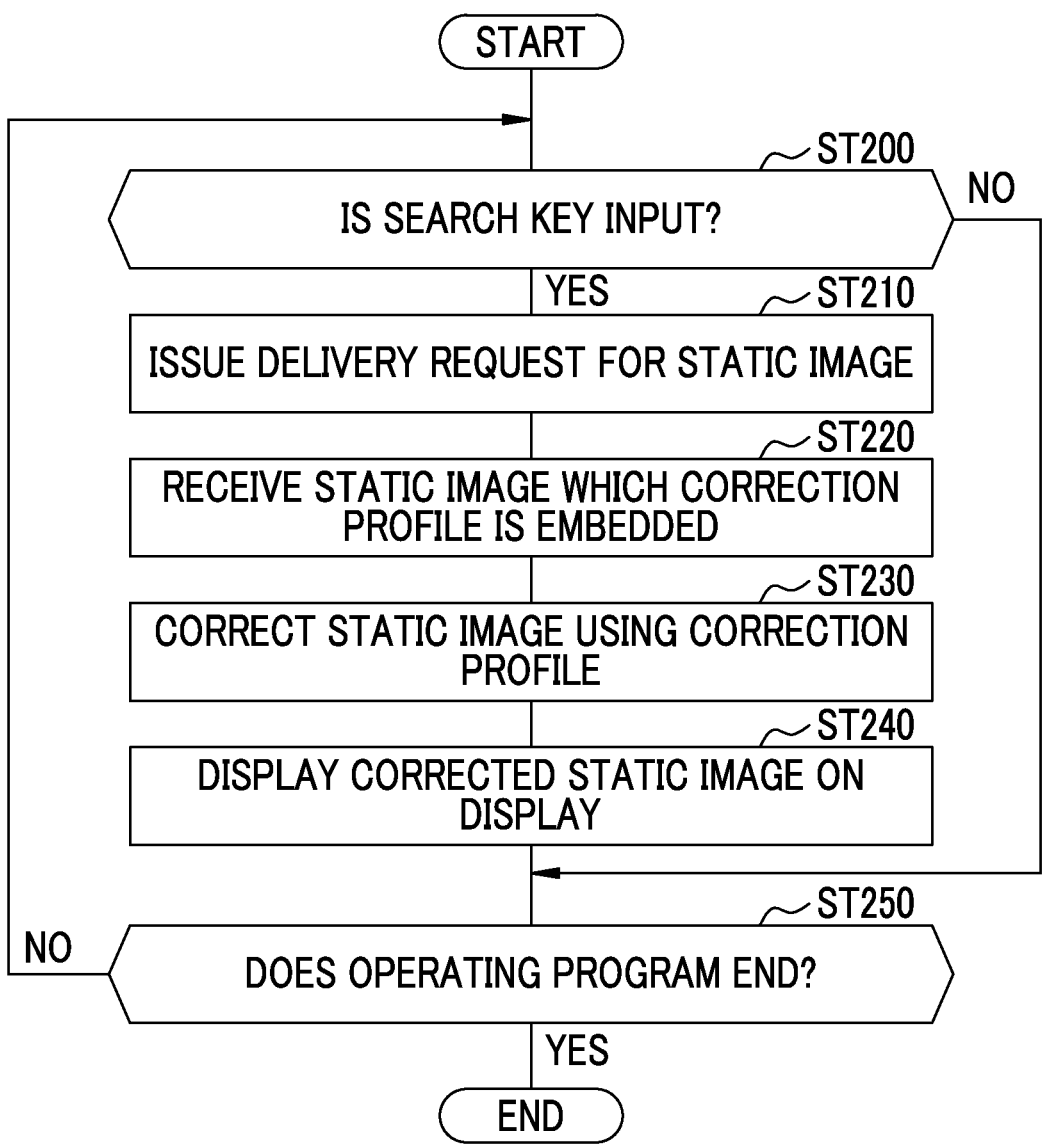
FIG. 21 is a flowchart showing the procedure of processing of the image display device.

In FIG. 21, the medical doctor of the diagnosis and treatment department inputs the search keys for a desired static image through the input unit 39 of the image display device 37 (YES in Step ST200). Accordingly, a delivery request for a static image is issued to the image storage server 36 from the receiving unit 115 (Step ST210).

A static image corresponding to the delivery request issued from the receiving unit 115 is searched in the image storage server 36. Then, the searched static image is transmitted to the image display device 37.

The static image delivered from the image storage server 36 is received by the receiving unit 115 (Step ST220, receiving step). A correction profile is embedded in this static image. The static image is output to the correction unit 116 from the receiving unit 115.

The static image is corrected using the correction profile, which is embedded in the static image, by the correction unit 116 (Step ST230, correction step). The tone of the static image is corrected by this correction. The corrected static image is output to the display control unit 117 from the correction unit 116, and is displayed on the display 38 by the display control unit 117 (Step ST240, display control step). These series of processing are repeatedly continued until the operating program 110 ends (the observation of the static image ends) (YES in Step ST250).

As described above, the processor device 12 embeds the correction profile, which is created according to the tone change-related information about a change in the tone of the static image, in the static image by the embedding unit 93 and outputs the static image in which the correction profile is embedded to the image storage server 36 by the output unit 94. Accordingly, resources are not consumed in processing not having much necessity unlike in the case of the related art where a correction profile is created whenever image pickup signals are updated according to a frame rate and the correction profile is applied to the image pickup signals in real time during endoscopy where a change in the tone of the image does not much cause a problem. Therefore, it is possible to allow a change in the tone of an image not to be noticeable with less wasteful processing.

Further, inconvenience where correction does not follow the update of image pickup signals and a correction delay occurs or a tone is excessively corrected due to the excessive effect of correction cannot occur unlike in the case of the related art where a correction profile is created whenever image pickup signals are updated according to a frame rate and the correction profile is applied to the image pickup signals in real time during endoscopy.

Since the image display device 37 receives the static image in which the correction profile is embedded by the receiving unit 115, corrects the static image by using the correction profile by the correction unit 116, and displays the corrected static image on the display 38 by the display control unit 117, an image where a change in tone is not noticeable can be displayed.

In a case where a plurality of static images obtained from single endoscopy performed for the same patient at the same date are arranged and displayed on the display 38 as shown in FIG. 19, are obtained before and after a change in the wavelength of illumination light, and are not corrected, there is a concern that a change in the tone of the image caused by a change in the wavelength of the illumination light may be recognized. However, since the static image, which is corrected using the correction profile created according to the wavelength change-related information, is displayed in this embodiment, there is no concern that a change in the tone of the image may be recognized.

Since the tones of the plurality of static images are unified, efficiency can be improved in a case where the plurality of static images are arranged and displayed to be compared and examined. For example, since the tones of lesions appearing in two static images may be different from each other in the two static images in a case where the tones of the two static images are not unified, the images need to be observed in consideration of a difference in tone. On the other hand, in a case where the tones of the two static images are unified, the images do not need to be observed in consideration of a difference in the tone of the lesion between the respective static images.

The tone change-related information is acquired only in a case where an instruction to perform an operation for recording a static image is given, and the correction profile is also created only in a case where an instruction for operation is given. Accordingly, there is no waste in processing.

Since the wavelength change-related information about a change in the wavelength of illumination light is used as the tone change-related information, a change in the tone of the image caused by a change in the wavelength of illumination light, which is an unavoidable problem, can be reliably corrected in a case where a semiconductor light source is used.

Since the correction profile includes the matrix coefficients CR1 to CR3, CG1 to CG3, and CB1 to CB3 (tone correction matrix C1) to be multiplied by the image pickup signals BIR, BIG, and BIB corresponding to the respective colors, respectively, as shown in Equation (2), the tone of the entire color gamut of the static image can be corrected. Further, since the tone correction matrix C1 can be embedded in, for example, a standard color profile, such as an ICC profile, the static image can be corrected with general-purpose processing corresponding to a standard color profile in the correction unit 116 of the image display device 37. For this reason, the operating program 110 serving as the base of the correction unit 116 can be relatively simply created.

Second Embodiment

The wavelength change-related information has been exemplified as the tone change-related information in the first embodiment. However, in a second embodiment shown in FIGS. 22 and 23, the spectral characteristic information of the color filters 85 to 87 of the image pickup element 46 (hereinafter, referred to as image pickup element-spectral characteristic information) and the spectral characteristic information of illumination light (hereinafter, referred to as illumination light-spectral characteristic information) are used as the tone change-related information instead of the wavelength change-related information.

The spectral characteristics of the color filters 85 to 87 are shown in FIG. 12. Further, the spectral characteristics of illumination light are shown in FIGS. 6 to 10. There is a deviation between the respective endoscopes 11A, 11B, . . . in terms of the spectral characteristics of the color filters 85 to 87. There is a deviation between the respective light source devices 13A, 13B, . . . even in terms of the spectral characteristics of illumination light. The tone of the image is also changed due to a deviation in the spectral characteristics of the color filters 85 to 87 and illumination light.

Figure 22:
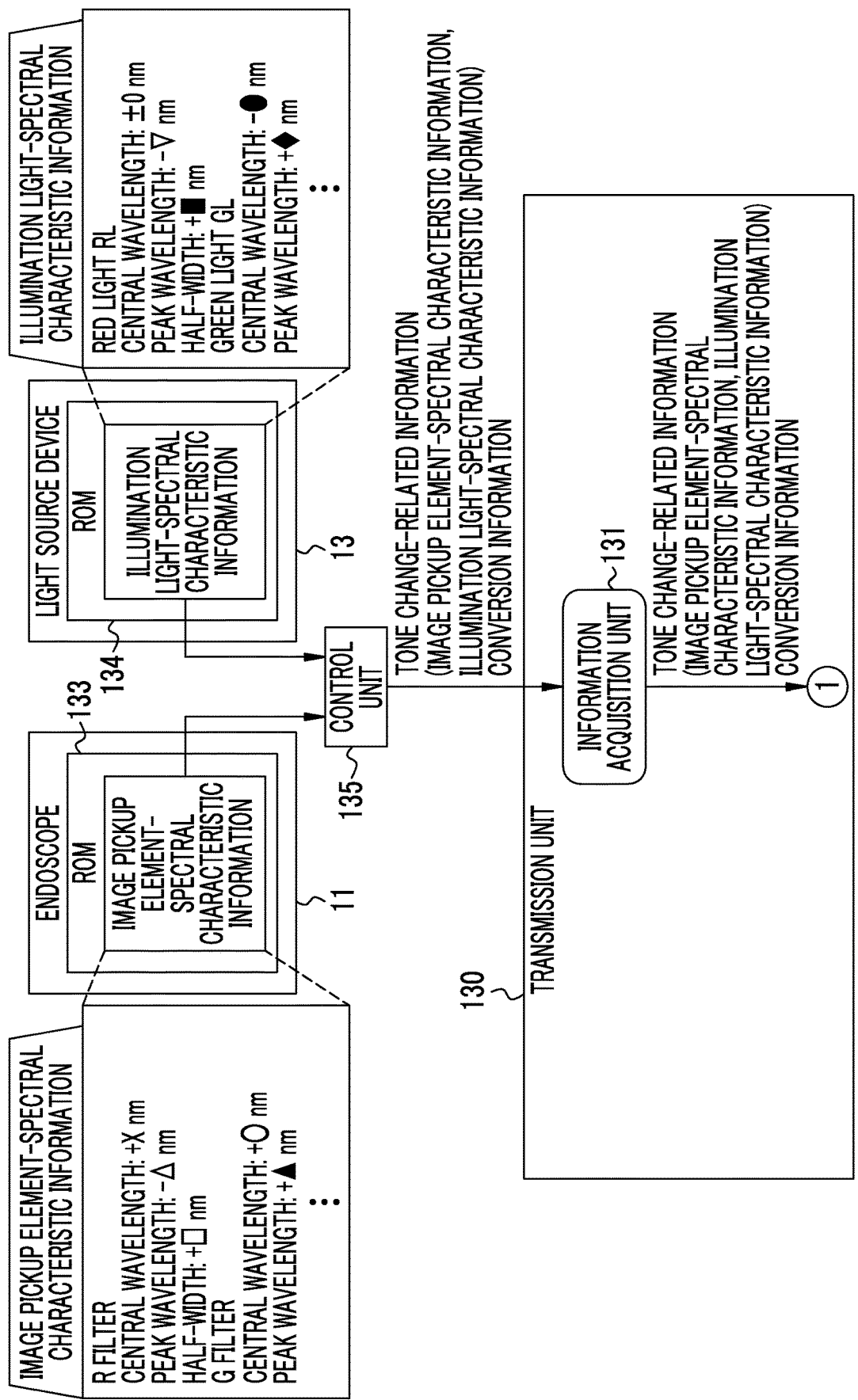
FIG. 22 is a block diagram of a transmission unit of a second embodiment.
Figure 23:
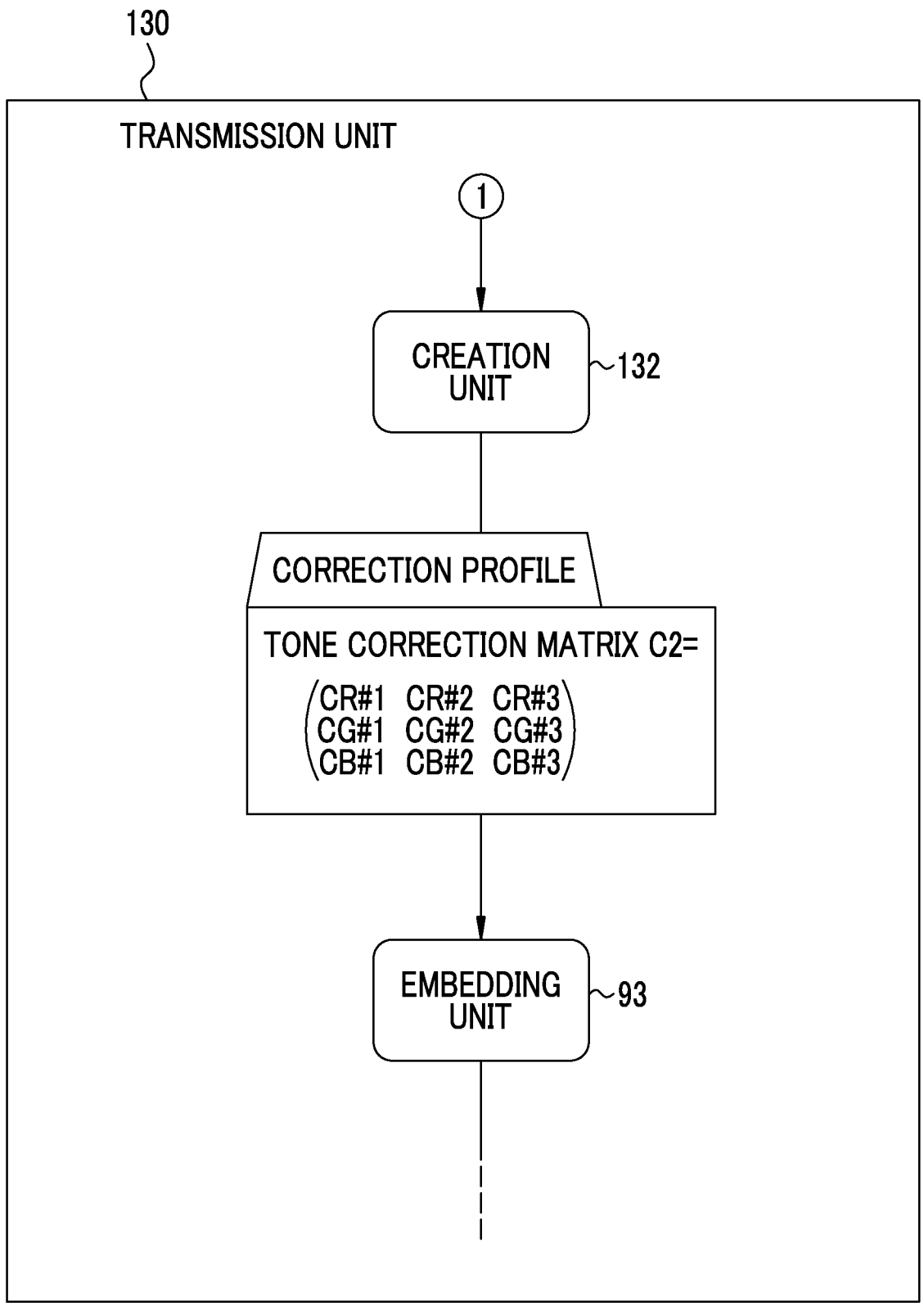
FIG. 23 is a block diagram of the transmission unit of the second embodiment.

Accordingly, a transmission unit 130 of the second embodiment shown in FIGS. 22 and 23 is provided with an information acquisition unit 131 that acquires the image pickup element-spectral characteristic information representing a deviation in the spectral characteristics of the color filters 85 to 87 and the illumination light-spectral characteristic information representing a deviation in the spectral characteristics of illumination light as the tone change-related information, and a creation unit 132 that creates a correction profile corresponding to the image pickup element-spectral characteristic information and the illumination light-spectral characteristic information.

Specifically, the image pickup element-spectral characteristic information can also be represented by the central wavelengths and peak wavelengths of the respective color filters 85 to 87 and the amounts of shift of half-widths of the respective color filters 85 to 87 from the reference of a half-width, and can also be represented as the relative spectral sensitivity values of the respective color filters 85 to 87 for every wavelength. Specifically, the illumination light-spectral characteristic information can also be represented by the central wavelengths and peak wavelengths of the respective color lights and the amounts of shift of half-widths of the respective color lights from the reference of a half-width, and can also be represented as the relative spectral emissivities of the respective color lights for every wavelength. The image pickup element-spectral characteristic information is measured in advance and is stored in an ROM 133 of an endoscope 11 at the time of shipment of the endoscope 11. Likewise, the illumination light-spectral characteristic information is measured in advance and is stored in an ROM 134 of a light source device 13 at the time of shipment of the light source device 13. Each of the ROMs 133 and 134 corresponds to a storage unit.

In a case where the endoscope 11 and the light source device 13 are connected to each other, the image pickup element-spectral characteristic information and the illumination light-spectral characteristic information are read out to a control unit 135 of a processor device from the respective ROMs 133 and 134 and are written in an ROM (not shown) of the control unit 135. The image pickup element-spectral characteristic information and the illumination light-spectral characteristic information are output to the information acquisition unit 131 from the control unit 135 as with the wavelength change-related information of the first embodiment only in a case where a recording instruction signal is input (in a case where an operator gives an instruction for operation).

The information acquisition unit 131 acquires the image pickup element-spectral characteristic information and the illumination light-spectral characteristic information, which are output from the control unit 135 and serve as the tone change-related information, and conversion information. The information acquisition unit 131 outputs the acquired illumination light-spectral characteristic information, the acquired image pickup element-spectral characteristic information, and the acquired conversion information to the creation unit 132. The conversion information in this case may be, for example, a function that uses the central wavelengths and peak wavelengths of the respective color filters 85 to 87 and the amounts of shift of half-widths of the respective color filters 85 to 87 from the reference of a half-width of the image pickup element-spectral characteristic information and the central wavelengths and peak wavelengths of the respective color lights and the amounts of shift of half-widths of the respective color lights from the reference of a half-width of the illumination light-spectral characteristic information as variables; and may be the amount of correction that is obtained from the relative spectral sensitivity values and the relative spectral emissivities for every wavelength.

The creation unit 132 obtains matrix coefficients CR #1, CR #2, CR #3, CG #1, CG #2, CG #3, CB #1, CB #2, and CB #3, which correspond to the respective colors of a red, a green, and a blue, on the basis of the image pickup element-spectral characteristic information, the illumination light-spectral characteristic information, and the conversion information output from the information acquisition unit 131, respectively; and creates a matrix of 3*3, in which these matrix coefficients are arranged as in the tone correction matrix C1 of the first embodiment, as a tone correction matrix C2. The tone correction matrix C2 can also be embedded in a standard color profile, such as an ICC profile, as with the tone correction matrix C1. The creation unit 132 outputs the created tone correction matrix C2 to the embedding unit 93 as the correction profile. Since subsequent processing is the same as that of the first embodiment, the description thereof will be omitted.

In this case, the correction unit 116 of the CPU 102 of the image display device 37 multiplies the tone correction matrix C2 and the static image BI together to calculate a corrected static image AI2 as shown in Equation (3).

$$AI2 = C2 \cdot BI \quad (3)$$

In a case where image pickup signals of the corrected static image AI2 corresponding to the respective colors of a red, a green, and a blue are denoted by AIR2, AIG2, and AIB2 as in the first embodiment, Equation (3) is rewritten as Equation (4).

$$\begin{pmatrix} AIR2 \\ AIG2 \\ AIB2 \end{pmatrix} = \begin{pmatrix} CR\#1 & CR\#2 & CR\#3 \\ CG\#1 & CG\#2 & CG\#3 \\ CB\#1 & CB\#2 & CB\#3 \end{pmatrix} \begin{pmatrix} BIR \\ BIG \\ BIB \end{pmatrix} \quad (4)$$

In this way, the matrix coefficients CR #1 to CR #3, CG #1 to CG #3, and CB #1 to CB #3 are also multiplied by the image pickup signals BIR, BIG, and BIB corresponding to the respective colors of a red, a green, and a blue, respectively.

Since the above-mentioned correction is performed on the static image BI, the static image AI2 of which a change in tone caused by a deviation in the spectral characteristics of the color filters 85 to 87 and the spectral characteristics of illumination light is corrected can be obtained.

For example, in a case where a plurality of static images obtained from a combination of the other endoscope 11 and the other light source device 13, such as the endoscope 11A and the light source device 13A and the endoscope 11B and the light source device 13B, are arranged and displayed on the display 38 and are not corrected, there is a concern that a change in the tone of the image caused by a deviation in the spectral characteristics of the color filters 85 to 87 and the spectral characteristics of illumination light may be recognized. However, since the static image, which is corrected using the correction profile created according to the image pickup element-spectral characteristic information and the illumination light-spectral characteristic information, is displayed in this embodiment, there is no concern that a change in the tone of the image may be recognized.

Since the image pickup element-spectral characteristic information and the illumination light-spectral characteristic information are measured in advance and are stored in the respective ROMs 133 and 134, labor for measuring these pieces of information every time can be saved and these pieces of information can be simply acquired by being just read out from the respective ROMs 133 and 134.

The first embodiment where the wavelength change-related information is used as the tone change-related information and the second embodiment where the image pickup element-spectral characteristic information and the illumination light-spectral characteristic information are used as the tone change-related information may be performed compositely. In this case, the corrected static image AI12 is represented by Equation (5).

$$AI12 = C1 \cdot C2 \cdot BI \quad (5)$$

In a case where image pickup signals of the corrected static image AI12 corresponding to the respective colors of a red, a green, and a blue are denoted by AIR12, AIG12, and AIB12, Equation (5) is rewritten as Equation (6).

$$\begin{pmatrix} AIR12 \\ AIG12 \\ AIB12 \end{pmatrix} = \begin{pmatrix} CR1 & CR2 & CR3 \\ CG1 & CG2 & CG3 \\ CB1 & CB2 & CB3 \end{pmatrix} \begin{pmatrix} CR\#1 & CR\#2 & CR\#3 \\ CG\#1 & CG\#2 & CG\#3 \\ CB\#1 & CB\#2 & CB\#3 \end{pmatrix} \begin{pmatrix} BIR \\ BIG \\ BIB \end{pmatrix} \quad (6)$$

In a case where the first embodiment where the wavelength change-related information is used as the tone change-related information and the second embodiment where the image pickup element-spectral characteristic information and the illumination light-spectral characteristic information are used as the tone change-related information are performed compositely, there is no concern that a change in the tone of the image caused by a change in the wavelength of illumination light and a change in the tone of the image caused by a deviation in the spectral characteristics of the color filters 85 to 87 and the spectral characteristics of illumination light may be recognized.

Third Embodiment

A correction profile has been embedded in the static image in the respective embodiments having been described above, but the tone change-related information is embedded in the static image in a third embodiment shown in FIGS. 24 to 27.

Figure 24:
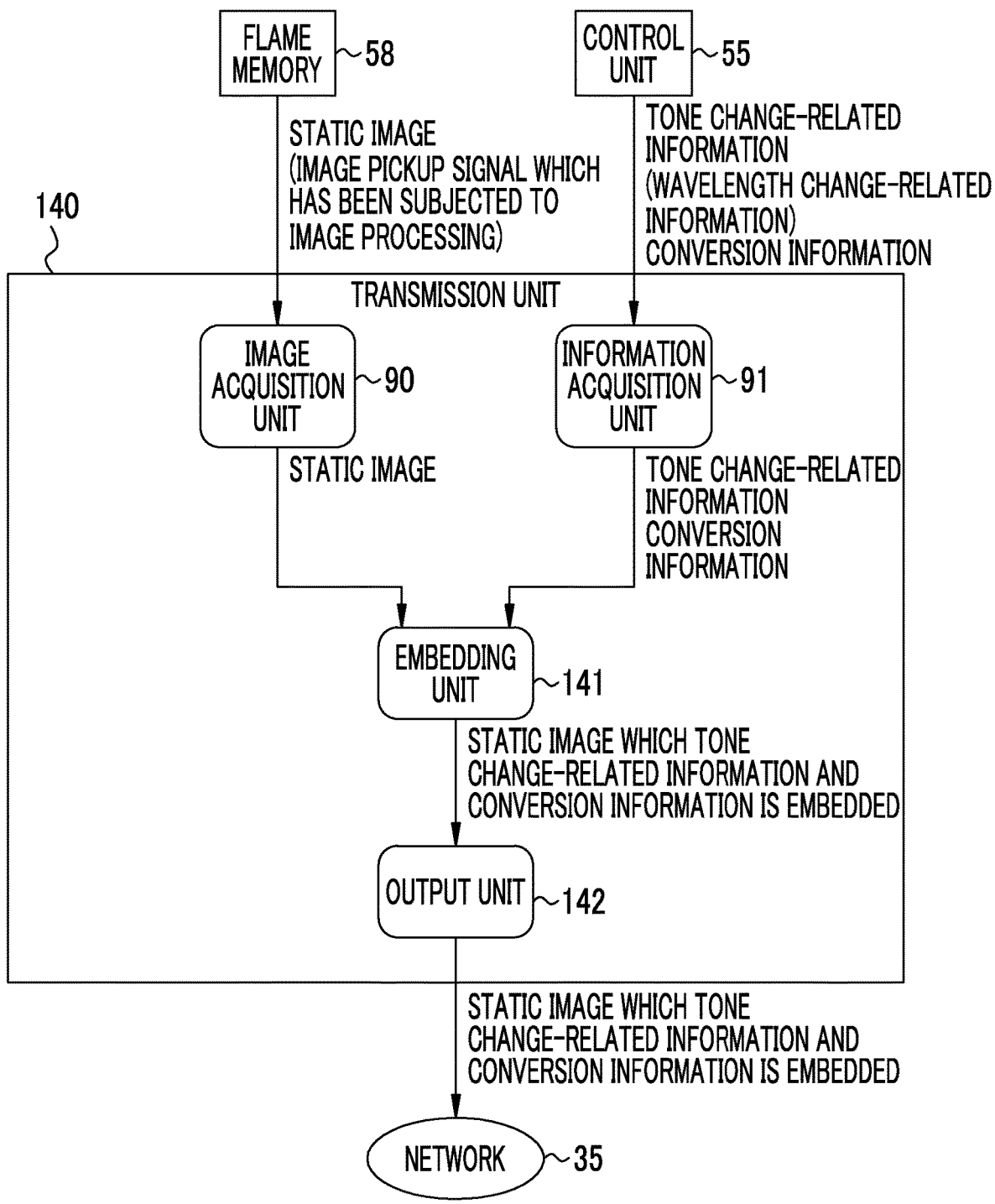
FIG. 24 is a block diagram of a transmission unit of a third embodiment.

In FIG. 24, a transmission unit 140 of the third embodiment is mainly different from the transmission unit 61 of the first embodiment in that the transmission unit 140 is not provided with the creation unit 92. In this case, the information acquisition unit 91 outputs the tone change-related information and the conversion information to the embedding unit 141. The embedding unit 141 embeds the tone change-related information and the conversion information, which are output from the information acquisition unit 91, in the static image, which is output from the image acquisition unit 90, instead of the correction profile of the first embodiment. The embedding unit 141 outputs the static image, in which the tone change-related information and the like are embedded, to an output unit 142. The output unit 142 outputs the static image, in which the tone change-related information and the like are embedded and which is received from the embedding unit 141, to the image storage server 36 through the network 35.

Figure 25:
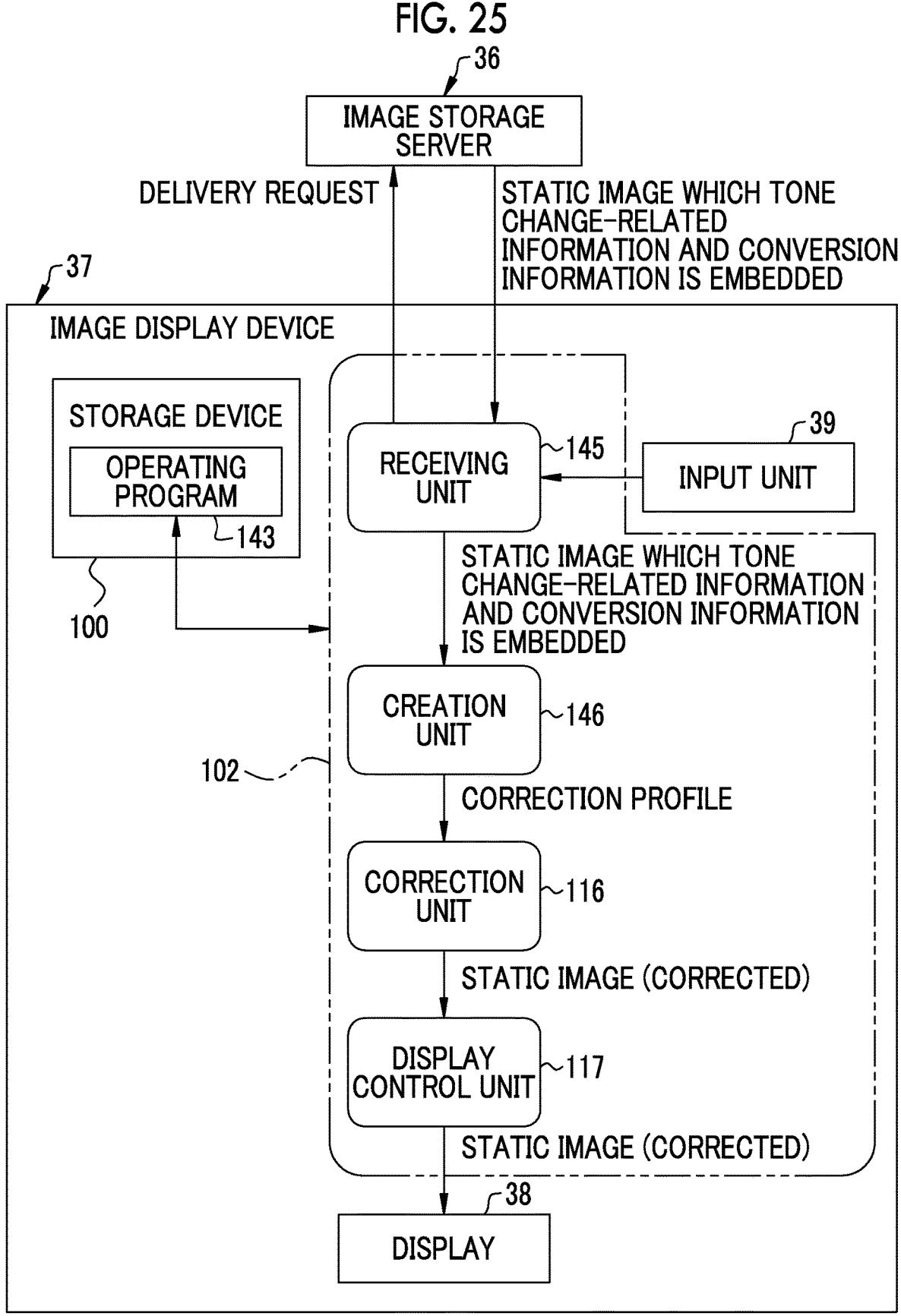
FIG. 25 is a block diagram of a CPU of a computer forming an image display device of the third embodiment.

In FIG. 25, an operating program 143 is stored in a storage device 100 of an image display device 37 of the third embodiment. In a case where the operating program 143 is started, a CPU 102 of the image display device 37 functions as the same creation unit 146 as the creation unit 92 of the first embodiment in addition to the same receiving unit 145 as the receiving unit 115 of the first embodiment, the correction unit 116, and the display control unit 117 in cooperation with the memory 101 and the like.

In this case, the receiving unit 145 receives the static image in which the tone change-related information and the like are embedded by the embedding unit 141 of the transmission unit 140 and which is transmitted from the image storage server 36. The receiving unit 145 outputs the received static image to the creation unit 146.

The creation unit 146 has a creation function to create a correction profile from the tone change-related information and the conversion information that are embedded in the static image. A method of creating the correction profile is the same as that of the creation unit 92 of the first embodiment. The creation unit 146 outputs the created correction profile to the correction unit 116. Since subsequent processing is the same as that of the first embodiment, the description thereof will be omitted.

Figure 26:
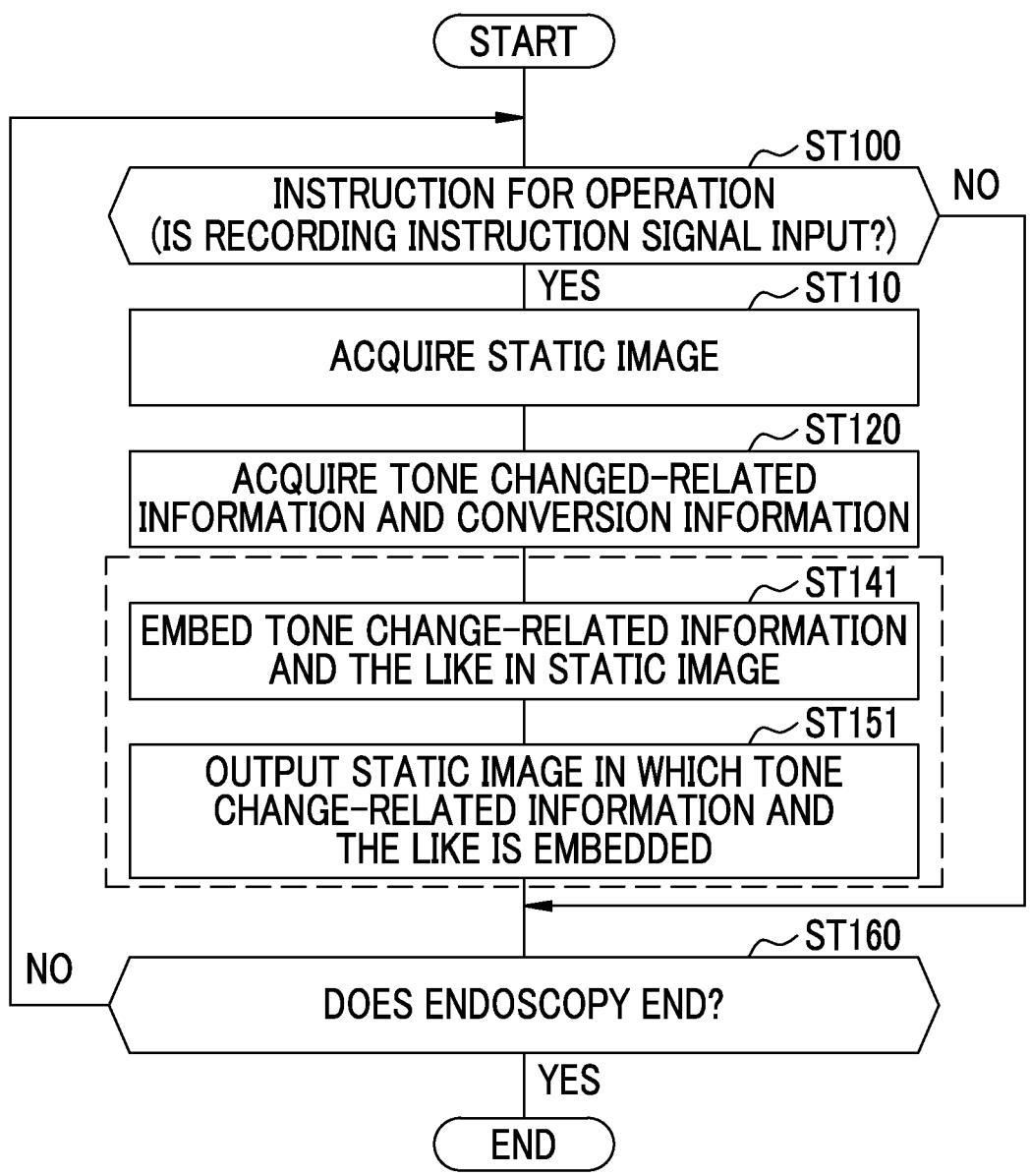
FIG. 26 is a flowchart showing the procedure of processing of a processor device of the third embodiment.

The flow of the processing of the second embodiment is shown in FIGS. 26 and 27. Portions surrounded by a broken line in FIGS. 26 and 27 are steps different from those of the first embodiment. The steps different from those of the first embodiment will be mainly described below.

First, as shown in FIG. 26, in the embedding unit 141 of the transmission unit 140, the tone change-related information and the like output from the information acquisition unit 91 are embedded in the static image output from the image acquisition unit 90 (Step ST141, embedding step). The static image in which the tone change-related information and the like are embedded is output to the image storage server 36 by the output unit 142 (Step ST151, output step).

Subsequently, as shown in FIG. 27, the static image, in which the tone change-related information and the like are embedded and which is delivered from the image storage server 36, is received by the receiving unit 145 (Step ST221, receiving step). The static image is output to the creation unit 146 from the receiving unit 145. A correction profile is created in the creation unit 146 according to the tone change-related information and the conversion information that are embedded in the static image (Step ST131, creation step).

As described above, the tone change-related information may be embedded in the static image by the embedding unit 141 instead of the correction profile and the static image in which the tone change-related information is embedded may be output to the image storage server 36 by the output unit 142. In this case, the creation unit 146 may be provided in the CPU 102 of the image display device 37 and a correction profile may be created in the image display device 37. Since the processor device does not need to be provided with a function to create a correction profile in this case, the configuration of the processor device can be simplified.

An example where the invention is applied to a case where the wavelength change-related information of the first embodiment is used as the tone change-related information has been described in FIGS. 24 to 27, but the invention may be applied to the second embodiment where the image pickup element-spectral characteristic information and the illumination light-spectral characteristic information are used as the tone change-related information.

The receiving unit of the CPU 102 of the image display device 37 may be adapted to receive both a static image in which a correction profile is embedded and a static image in which the tone change-related information is embedded. In this case, the creation unit 146 does not operate in a case where the static image in which the correction profile is embedded is received by the receiving unit, and the creation unit 146 operates to create a correction profile only in a case where the static image in which the tone change-related information is embedded is received by the receiving unit.

The tone correction matrices C1 and C2 have been exemplified as the correction profile in the respective embodiments having been described above, but a white balance correction coefficient, a gradation conversion coefficient, a three-dimensional look-up table, and the like may be included in the correction profile in addition to the tone correction matrices C1 and C2.

The color filter is not limited to a combination of primary colors of a red, a green, and a blue described in the respective embodiments having been described above, and may employ a combination of complementary colors of a cyan, a magenta, and a yellow. Further, the light source is not limited to the LED described in the respective embodiments having been described above, and may be a laser diode (LD). Furthermore, the invention is effective even in a case where a xenon lamp or a metal halide lamp in the related art is used as the light source.

The control unit may have the functions of the image acquisition unit, the creation unit, the embedding unit, and the output unit.

An aspect where the static image transmitted from the processor device 12 is stored in the image storage server 36 and the static image is delivered to the image display device 37 from the image storage server 36 has been exemplified in the respective embodiments having been described above. However, the image storage server 36 may be removed, the static image may be directly transmitted to the image display device 37 from the processor device 12, and the static image may be stored in the storage device 100 of the image display device 37.

Further, a range covered by the image storage server 36 is not limited to one medical facility and may correspond to a plurality of medical facilities. In this case, a wide area network (WAN) is used as the network 35.

The computer forming the image display device 37 is not limited to a desktop computer. The computer may be a laptop computer or a tablet computer.

For example, the hardware structure of processing units for performing various kinds of processing in the respective embodiments having been described above, such as the image acquisition unit 90, the information acquisition units 91 and 131, the creation units 92, 132, and 146, the embedding units 93 and 141, the output units 94 and 142, the receiving units 115 and 145, the correction unit 116, and the display control unit 117, is various processors to be described below.

Various processors include a CPU, a programmable logic device (PLD), a dedicated electrical circuit, and the like. The CPU is a general-purpose processor that functions as various processing units by executing software (program) as well known. The PLD is a processor of which circuit configuration can be changed after manufacture, such as a field programmable gate array (FPGA). A dedicated electrical circuit is a processor having circuit configuration designed exclusively to perform specific processing, such as an application specific integrated circuit (ASIC).

One processing unit may be formed of one of these various processors, and may be formed of a combination of two or more same kind or different kinds of processors (for example, a plurality of FPGAs or a combination of a CPU and an FPGA). Further, a plurality of processing units are formed of one processor. As an example where a plurality of processing units are formed of one processor, first, there is an aspect where one processor is formed of a combination of one or more CPUs and software and this processor functions as a plurality of processing units. Second, there is an aspect where a processor fulfilling the functions of the entire system including a plurality of processing units by one integrated circuit (IC) chip as typified by System On Chip (SoC) or the like is used. As described above, various processing units are formed using one or more of the above-mentioned various processors as hardware structure.

In addition, the hardware structure of these various processors is more specifically electrical circuitry in which circuit elements, such as semiconductor elements, are combined.

A processor device according to additional claim 1, an endoscope system according to additional claim 2, and an image display device according to additional claim 3 to be described below can be grasped from the above description.

[Additional claim 1]

A processor device to which an endoscope irradiating an object to be observed with illumination light supplied from a light source is to be connected, comprising:

an image acquisition processor that acquires a static image of the object to be observed picked up according to an operator's instruction for operation;

an embedding processor that embeds tone change-related information about a change in a tone of the static image or a correction profile, which is created according to the tone change-related information and is used to correct a change in the tone, in the static image; and an output processor that outputs the static image, in which the tone change-related information or the correction profile is embedded, to the outside.

[Additional claim 2]

An endoscope system comprising:

an endoscope that irradiates an object to be observed with illumination light supplied from a light source;

a light source device in which the light source is built; and a processor device to which the endoscope and the light source device are to be connected, wherein the processor device includes an image acquisition processor that acquires a static image of the object to be observed picked up according to an operator's instruction for operation, an embedding processor that embeds tone change-related information about a change in a tone of the static image or a correction profile, which is created according to the tone change-related information and is used to correct a change in the tone, in the static image, and an output processor that outputs the static image, in which the tone change-related information or the correction profile is embedded, to the outside.

[Additional claim 3]

An image display device comprising:

a receiving unit that receives a static image in which tone change-related information about a change in a tone of the static image or a correction profile created according to the tone change-related information and used to correct a change in the tone is embedded;

a creation processor that creates the correction profile from the tone change-related information in a case where the static image received by the receiving processor is the static image in which the tone change-related information is embedded;

a correction processor that performs the correction on the static image by using the correction profile; and a display control processor that controls display of the static image, on which the correction has been performed, on a display unit.

The invention can also be applied to a fiberscope that guides the image of an object to be observed to an eyepiece part by an image guide, a processor device to which an ultrasonic endoscope including a distal end part in which an ultrasonic transducer is built in addition to an image pickup element is to be connected, and an endoscope system.

It goes without saying that the invention is not limited to the respective embodiments having been described above and can employ various configurations without departing from the scope of the invention. In addition, the invention covers not only a program but also a storage medium that stores a program.

EXPLANATION OF REFERENCES 10, 10A, 10B: endoscope system
11, 11A, 11B: endoscope
12, 12A, 12B: processor device
13, 13A, 13B: light source device
14: monitor
15: input unit
16: insertion part
17: operation part
18: universal cord
19: distal end part
20: bendable part
21: flexible tube part
22: angle knob
23: release button
24: air/water supply button
25: forceps port
26: connector
26A: connector for communication
26B: connector for light source
30: observation window
31: illumination window
32: air/water supply nozzle
33: forceps outlet
35: network
36: image storage server
37: image display device
38: display
39: input unit
45: light guide
46: image pickup element
46A: image pickup surface
47: image pickup control unit
48: signal transmission/reception unit
49: irradiation lens
50: objective optical system
55, 135: control unit
56: signal transmission/reception unit
57: DSP
58: frame memory
59: image processing unit
60: display control unit
61, 130, 140: transmission unit
65: light source unit
66: light source control unit
70: red LED
71: green LED
72: blue LED
73: violet LED
74: light source optical system
75 to 78: collimating lens
79 to 81: dichroic mirror
82: condenser lens 85: red filter
86: green filter
87: blue filter
90: image acquisition unit
91, 131: information acquisition unit
92, 132, 146: creation unit
93, 141: embedding unit
94, 142: output unit
100: storage device
101: memory
102: CPU
103: communication unit
104: data bus
110, 143: operating program
115, 145: receiving unit
116: correction unit
117: display control unit
133, 134: ROM
RL: red light
GL: green light
BL: blue light
VL: violet light
ML: mixed light
IR: the amount of current of red LED
IG: the amount of current of green LED
IB: the amount of current of blue LED
IV: the amount of current of violet LED
F(IR): red conversion function
F(IG): green conversion function
F(IB, IV): blue conversion function
CR1 to CR3, CR #1 to CR #3: red matrix coefficient
CG1 to CG3, CG #1 to CG #3: green matrix coefficient
CB1 to CB3, CB #1 to CB #3: blue matrix coefficient
C1, C2: tone correction matrix
ST100 to ST160, ST200 to ST250: Step

What is claimed is:

1. A processor device to be connected with an endoscope irradiating an object to be observed with illumination light supplied from a light source, and to output a video of the object to be observed to a monitor, the video being picked up by the endoscope, comprising:
   a processor configured to:
      acquire a static image of the object to be observed only when an operator gives an instruction for operation for recording the static image while observing the video of the object to be observed;
      acquire tone change-related information about a change in a tone of the static image from a reference tone only in a case where the instruction for operation is given;
      when the tone of the static image deviates from the reference tone, create a correction profile according to the tone change-related information to correct the change in the tone of the static image only in a case where the instruction for operation is given;
      embed the tone change-related information or the correction profile in the static image; and
      output the static image, in which the tone change-related information or the correction profile is embedded.

2. The processor device according to claim 1, wherein the tone change-related information is wavelength change-related information about a change in a wavelength of the illumination light depending on a temperature of the light source.

3. The processor device according to claim 1, wherein the tone change-related information is spectral characteristic information of the illumination light and spectral characteristic information of a color filter of an image pickup element picking up an image of the object to be observed.

4. The processor device according to claim 3, wherein the spectral characteristic information of the illumination light and the spectral characteristic information of the color filter are measured in advance and are stored in a memory.

5. The processor device according to claim 1, wherein the correction profile includes matrix coefficients to be multiplied by image pickup signals that correspond to a plurality of colors and are output from an image pickup element picking up an image of the object to be observed.

6. The processor device according to claim 1, wherein the correction profile is embedded in a standard color profile.

7. The processor device according to claim 1, wherein the light source is a light-emitting diode.

8. The processor device according to claim 1, wherein the endoscope has a release button configured to be operated to be pressed in a case where the static image of the object to be observed is to be recorded, and the instruction for operation is generated by operation of the release button.

9. The processor device according to claim 1, further comprising a frame memory for storing image pickup signals written therein, the image pickup signals having a frame rate,
   wherein the processor is further configured to:
      output the image pickup signals for display of an image of the object as the video on a monitor;
      acquire the static image by temporarily stopping rewriting of the image pickup signals in the frame memory; and
      reading out from the frame memory the image pickup signals of which the rewriting was temporarily stopped.

10. A method of operating a processor device to be connected with an endoscope irradiating an object to be observed with illumination light supplied from a light source, and to output a video of the object to be observed to a monitor, the video being picked up by the endoscope, the method comprising:
   an image acquisition step of acquiring a static image of the object to be observed only when an operator gives an instruction for operation for recording the static image while observing the video of the object to be observed;
   a tone change-related information step of acquiring tone change-related information about a change in a tone of the static image from a reference tone only in a case where the instruction for operation is given;
   when the tone of the static image deviates from the reference tone, a correction profile step of creating a correction profile according to the tone change-related information to correct the change in tone of the static image only in a case where the instruction for operation is given;
   an embedding step of embedding the tone change-related information or the correction profile in the static image; and
   an output step of outputting the static image, in which the tone change-related information or the correction profile is embedded.

11. The method according to claim 10, wherein the endoscope has a release button configured to be operated to be pressed in a case where the static image of the object to be observed is to be recorded, and the instruction for operation is generated by operation of the release button.

12. The method according to claim 10, wherein the processor device further comprises a frame memory for storing image pickup signals written therein, the image pickup signals having a frame rate, the method further comprising:
 a video output step of outputting the image pickup signals for display of an image of the object as the video on a monitor, wherein the static image is acquired by temporarily stopping rewriting of the image pickup signals in the frame memory; and
 a reading out step of reading out from the frame memory the image pickup signals of which the rewriting was temporarily stopped.

13. An endoscope system comprising:
 an endoscope that irradiates an object to be observed with illumination light supplied from a light source;
 a light source device in which the light source is built; and
 a processor device to which the endoscope and the light source device are to be connected,
 wherein the processor device includes a processor configured to:
  acquire a static image of the object to be observed only when an operator gives an instruction for operation for recording the static image while observing the video of the object to be observed,
  acquire tone change-related information about a change in a tone of the static image from a reference tone only in a case where the instruction for operation is given;
  when the tone of the static image deviates from the reference tone, create a correction profile according to the tone change-related information to correct the change in tone of the static image only in a case where the instruction for operation is given;
  embed the tone change-related information or the correction profile in the static image, and
  output the static image, in which the tone change-related information or the correction profile is embedded.

14. The endoscope system according to claim 13, wherein the endoscope has a release button configured to be operated to be pressed in a case where the static image of the object to be observed is to be recorded, and the instruction for operation is generated by operation of the release button.

15. The endoscope system of claim 13, wherein the processor device further includes a frame memory for storing image pickup signals written therein, the image pickup signals having a frame rate, wherein the processor is further configured to:
 output the image pickup signals for display of an image of the object as the video on a monitor;
 acquire the static image by temporarily stopping rewriting of the image pickup signals in the frame memory; and
 reading out from the frame memory the image pickup signals of which the rewriting was temporarily stopped.

16. An image display device comprising a processor configured to:
 receive a static image in which tone change-related information about a change in a tone of the static image from a reference tone or a correction profile created according to the tone change-related information and used to correct the change in the tone of the static image is embedded only in a case where an instruction for operation for recording the static image is given;
 create the correction profile from the tone change-related information in a case where the static image received by a receiving unit is the static image in which the tone change-related information is embedded;
 perform the correction on the static image by using the correction profile in a case where the correction profile is created; and
 control display of the static image, on which the correction has been performed, on a display unit.

17. A method of operating an image display device, the method comprising:
 a receiving step of receiving a static image in which tone change-related information about a change in a tone of the static image from a reference tone or a correction profile created according to the tone change-related information and used to correct the change in the tone of the static image is embedded, only in a case where an instruction for operation for recording the static image is given;
 a creation step of creating the correction profile from the tone change-related information in a case where the static image received in the receiving step is the static image in which the tone change-related information is embedded;
 a correction step of performing the correction on the static image by using the correction profile in a case where the correction profile is created; and
 a display control step of controlling display of the static image, on which the correction has been performed, on a display unit.

* * * * *